(12) United States Patent
Foltz et al.

(10) Patent No.: US 7,572,444 B2
(45) Date of Patent: Aug. 11, 2009

(54) BINDING PROTEINS SPECIFIC FOR HUMAN MATRIPTASE

(75) Inventors: Ian Foltz, Burnaby (CA); Chadwick King, North Vancouver (CA); Peter Koon Bong Ling, Vancouver (CA); Jaspal Singh Kang, Surrey (CA); Kathy Manchulenko, Port Coquitlam (CA); Francine Chen, San Francisco, CA (US); Caroline Darne Scatena, Alameda, CA (US); Bruce A. Keyt, Hillsborough, CA (US); Edwin Madison, San Francisco, CA (US); Wayne R. Godfrey, Bainbridge Island, WA (US); Stanislaw K. Morkowski, Lake Forest Park, WA (US); Jennifer H. Richardson, Fremont, CA (US)

(73) Assignees: Amgen Fremont Inc., Fremont, CA (US); Dendreon Corporation, Seattle, WA (US)

( * ) Notice: Subject to any disclaimer, the term of this patent is extended or adjusted under 35 U.S.C. 154(b) by 0 days.

(21) Appl. No.: 11/303,608

(22) Filed: Dec. 16, 2005

(65) Prior Publication Data
US 2006/0171884 A1 Aug. 3, 2006

Related U.S. Application Data

(60) Provisional application No. 60/637,859, filed on Dec. 20, 2004, provisional application No. 60/706,467, filed on Aug. 8, 2005.

(51) Int. Cl.
*A61K 39/395* (2006.01)
*A61K 51/00* (2006.01)
*C07H 21/04* (2006.01)
*C12N 5/06* (2006.01)
*C12P 21/06* (2006.01)

(52) U.S. Cl. ............... 424/133.1; 424/1.49; 424/155.1; 435/320.1; 435/338; 435/69.1; 536/23.53

(58) Field of Classification Search .............. 424/133.1, 424/1.49, 155.1; 435/320.1, 338, 69.1; 536/23.53
See application file for complete search history.

(56) References Cited

U.S. PATENT DOCUMENTS 6,677,377 B2   1/2004   Lin et al.
7,022,821 B1 *  4/2006  O'Brien et al. .......... 530/388.1

FOREIGN PATENT DOCUMENTS

WO        WO 01/29056        4/2001

OTHER PUBLICATIONS

Search output from ATCC website for sc95/96 and sc136 (pp. 1-2).*
Fundamental Immunology 242 (William E. Paul, M.D. ed., 3d ed. 1993).*
Benaud et al. (Eur. J. Biochem. 268:1439-1447 (2001).*
Green (J. Immunol. Methods 231:11-23 (1999).*
Sun (Breast Cancer Research Program grant award-year 2001 (Abstract of Grant Award (pp. 1-3); Sun II).*
Lin, et al., "Characterization of a Novel, Membrane-bound, 80-kDa Matrix-degrading Protease from Human Breast Cancer Cells," Journal of Biological Chemistry, vol. 272, No. 14, pp. 9147-9152 (Apr. 4, 1997).
Sun, et al., "Potent and Selective Inhibition of Membrane-Type Serine Protease 1 by Human Single-Chain Antibodies," *Biochemistry* 2003, 42, pp. 892-900.
Foltz, Ian et al., "Generation of a Fully Human High Affinity Neutralizing Antibody Against MT-SP1/Matriptase and Its Potential Role for the Treatment of B Cell Lymphoma," Blood, vol. 106, 2005, p. 284B.
Lin, Chen-Yong et al., "Purification and Characterization of a Complex Containing Matriptase and a Kunitz-type Serine Protease Inhibitor from Human Milk," The Journal of Biological Chemistry, vol. 274, No. 26, Jun. 25, 1999, pp. 18237-18242.
Takeuchi, Toshihiko et al., "Cellular Localization of Membrane-type Serine Protease 1 and Identification of Protease-activated Receptor-2 and Single-chain Urokinase-type Plasminogen Activator as Substrates," The Journal of Biological Chemistry, vol. 275, No. 34, Aug. 25, 2000, pp. 26333-26342.
Takeuchi, Toshihiko et al., "Reverse biochemistry: Use of macromolecular protease inhibitors to dissect complex biological processes and identify a membrane-type serine protease in epithelial cancer and normal tissue," Proc. Natl. Acad. Sci., vol. 96, Sep. 1999, pp. 11054-11061.
International Search Report dated Jul. 3, 2006 for International Application No. PCT/US2005/045755.
Lee et al., Activation of hepatocyte growth factor and urokinase/plasminogen activator by matriptase, an epithelial membrane serine protease, *J Biol Chem.* (2000);275(47):36720-5.
ROC (Taiwan) Search Report for Patent Application No. 094144958.
ROC (Taiwan) Search Report for Patent Application No. 094144958, Jan. 31, 2008.

* cited by examiner

*Primary Examiner*—David J. Blanchard
*Assistant Examiner*—Lynn Bristol
(74) *Attorney, Agent, or Firm*—Knobbe, Martens, Olson & Bear LLP

(57) ABSTRACT

Binding proteins, such as fully human monoclonal antibodies and fragments thereof, directed to the antigen Matriptase and uses of such binding proteins are disclosed. Nucleotide sequences encoding, and amino acid sequences comprising heavy and light chain immunoglobulin molecules capable of binding to Matriptase are also disclosed. The invention also discloses cell lines expressing such immunoglobulin molecules and monoclonal antibodies to Matriptase. The antibodies can be used to detect, prevent, and treat diseases such as cancer.

17 Claims, 9 Drawing Sheets

```
SEQUENCE LISTING

<160> NUMBER OF SEQ ID NOS: 12

<210> SEQ ID NO 1
<211> LENGTH: 855
<212> TYPE: PRT
<213> ORGANISM: Homo sapiens

<400> SEQUENCE: 1

Met Gly Ser Asp Arg Ala Arg Lys Gly Gly Gly Pro Lys Asp Phe
 1               5                  10                  15

Gly Ala Gly Leu Lys Tyr Asn Ser Arg His Glu Lys Val Asn Gly Leu
                20                  25                  30

Glu Glu Gly Val Glu Phe Leu Pro Val Asn Asn Val Lys Lys Val Glu
            35                  40                  45

Lys His Gly Pro Gly Arg Trp Val Val Leu Ala Ala Val Leu Ile Gly
        50                  55                  60

Leu Leu Leu Val Leu Leu Gly Ile Gly Phe Leu Val Trp His Leu Gln
65                  70                  75                  80

Tyr Arg Asp Val Arg Val Gln Lys Val Phe Asn Gly Tyr Met Arg Ile
                85                  90                  95

Thr Asn Glu Asn Phe Val Asp Ala Tyr Glu Asn Ser Asn Ser Thr Glu
            100                 105                 110

Phe Val Ser Leu Ala Ser Lys Val Lys Asp Ala Leu Lys Leu Leu Tyr
        115                 120                 125

Ser Gly Val Pro Phe Leu Gly Pro Tyr His Lys Glu Ser Ala Val Thr
    130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
            180                 185                 190

Val Thr Ser Val Val Ala Phe Pro Thr Asp Ser Lys Thr Val Gln Arg
        195                 200                 205

Thr Gln Asp Asn Ser Cys Ser Phe Gly Leu His Ala Arg Gly Val Glu
    210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
```

-continued

```
                260                 265                 270
Ser Asp Leu Val Thr Val Tyr Asn Thr Leu Ser Pro Met Glu Pro His
            275                 280                 285
Ala Leu Val Gln Leu Cys Gly Thr Tyr Pro Ser Tyr Asn Leu Thr
    290                 295                 300
Phe His Ser Ser Gln Asn Val Leu Leu Ile Thr Leu Ile Thr Asn Thr
305                 310                 315                 320
Glu Arg Arg His Pro Gly Phe Glu Ala Thr Phe Phe Gln Leu Pro Arg
                325                 330                 335
Met Ser Ser Cys Gly Gly Arg Leu Arg Lys Ala Gln Gly Thr Phe Asn
            340                 345                 350
Ser Pro Tyr Tyr Pro Gly His Tyr Pro Pro Asn Ile Asp Cys Thr Trp
    355                 360                 365
Asn Ile Glu Val Pro Asn Asn Gln His Val Lys Val Arg Phe Lys Phe
370                 375                 380
Phe Tyr Leu Leu Glu Pro Gly Val Pro Ala Gly Thr Cys Pro Lys Asp
385                 390                 395                 400
Tyr Val Glu Ile Asn Gly Glu Lys Tyr Cys Gly Glu Arg Ser Gln Phe
                405                 410                 415
Val Val Thr Ser Asn Ser Asn Lys Ile Thr Val Arg Phe His Ser Asp
            420                 425                 430
Gln Ser Tyr Thr Asp Thr Gly Phe Leu Ala Glu Tyr Leu Ser Tyr Asp
    435                 440                 445
Ser Ser Asp Pro Cys Pro Gly Gln Phe Thr Cys Arg Thr Gly Arg Cys
    450                 455                 460
Ile Arg Lys Glu Leu Arg Cys Asp Gly Trp Ala Asp Cys Thr Asp His
465                 470                 475                 480
Ser Asp Glu Leu Asn Cys Ser Cys Asp Ala Gly His Gln Phe Thr Cys
                485                 490                 495
Lys Asn Lys Phe Cys Lys Pro Leu Phe Trp Val Cys Asp Ser Val Asn
            500                 505                 510
Asp Cys Gly Asp Asn Ser Asp Glu Gln Gly Cys Ser Cys Pro Ala Gln
    515                 520                 525
Thr Phe Arg Cys Ser Asn Gly Lys Cys Leu Ser Lys Ser Gln Gln Cys
    530                 535                 540
Asn Gly Lys Asp Asp Cys Gly Asp Gly Ser Asp Glu Ala Ser Cys Pro
545                 550                 555                 560
Lys Val Asn Val Val Thr Cys Thr Lys His Thr Tyr Arg Cys Leu Asn
                565                 570                 575
Gly Leu Cys Leu Ser Lys Gly Asn Pro Glu Cys Asp Gly Lys Glu Asp
            580                 585                 590
Cys Ser Asp Gly Ser Asp Glu Lys Asp Cys Asp Cys Gly Leu Arg Ser
    595                 600                 605
Phe Thr Arg Gln Ala Arg Val Val Gly Gly Thr Asp Ala Asp Glu Gly
    610                 615                 620
Glu Trp Pro Trp Gln Val Ser Leu His Ala Leu Gly Gln Gly His Ile
625                 630                 635                 640
Cys Gly Ala Ser Leu Ile Ser Pro Asn Trp Leu Val Ser Ala Ala His
                645                 650                 655
Cys Tyr Ile Asp Asp Arg Gly Phe Arg Tyr Ser Asp Pro Thr Gln Trp
            660                 665                 670
Thr Ala Phe Leu Gly Leu His Asp Gln Ser Gln Arg Ser Ala Pro Gly
    675                 680                 685
```

```
Val Gln Glu Arg Arg Leu Lys Arg Ile Ile Ser His Pro Phe Phe Asn
    690                 695                 700
Asp Phe Thr Phe Asp Tyr Asp Ile Ala Leu Leu Glu Leu Glu Lys Pro
705                 710                 715                 720
Ala Glu Tyr Ser Ser Met Val Arg Pro Ile Cys Leu Pro Asp Ala Ser
                    725                 730                 735
His Val Phe Pro Ala Gly Lys Ala Ile Trp Val Thr Gly Trp Gly His
                740                 745                 750
Thr Gln Tyr Gly Gly Thr Gly Ala Leu Ile Leu Gln Lys Gly Glu Ile
            755                 760                 765
Arg Val Ile Asn Gln Thr Thr Cys Glu Asn Leu Leu Pro Gln Gln Ile
770                 775                 780
Thr Pro Arg Met Met Cys Val Gly Phe Leu Ser Gly Gly Val Asp Ser
785                 790                 795                 800
Cys Gln Gly Asp Ser Gly Gly Pro Leu Ser Ser Val Glu Ala Asp Gly
                805                 810                 815
Arg Ile Phe Gln Ala Gly Val Val Ser Trp Gly Asp Gly Cys Ala Gln
                820                 825                 830
Arg Asn Lys Pro Gly Val Tyr Thr Arg Leu Pro Leu Phe Arg Asp Trp
                835                 840                 845
Ile Lys Glu Asn Thr Gly Val
    850                 855

<210> SEQ ID NO 2
<211> LENGTH: 241
<212> TYPE: PRT
<213> ORGANISM: Homo sapiens

<400> SEQUENCE: 2

Val Val Gly Gly Thr Asp Ala Asp Glu Gly Glu Trp Pro Trp Gln Val
1               5                   10                  15
Ser Leu His Ala Leu Gly Gln Gly His Ile Cys Gly Ala Ser Leu Ile
            20                  25                  30
Ser Pro Asn Trp Leu Val Ser Ala Ala His Cys Tyr Ile Asp Asp Arg
        35                  40                  45
Gly Phe Arg Tyr Ser Asp Pro Thr Gln Trp Thr Ala Phe Leu Gly Leu
    50                  55                  60
His Asp Gln Ser Gln Arg Ser Ala Pro Gly Val Gln Glu Arg Arg Leu
65                  70                  75                  80
Lys Arg Ile Ile Ser His Pro Phe Phe Asn Asp Phe Thr Phe Asp Tyr
                85                  90                  95
Asp Ile Ala Leu Leu Glu Leu Glu Lys Pro Ala Glu Tyr Ser Ser Met
            100                 105                 110
Val Arg Pro Ile Cys Leu Pro Asp Ala Ser His Val Phe Pro Ala Gly
        115                 120                 125
Lys Ala Ile Trp Val Thr Gly Trp Gly His Thr Gln Tyr Gly Gly Thr
    130                 135                 140
Gly Ala Leu Ile Leu Gln Lys Gly Glu Ile Arg Val Ile Asn Gln Thr
145                 150                 155                 160
Thr Cys Glu Asn Leu Leu Pro Gln Gln Ile Thr Pro Arg Met Met Cys
                165                 170                 175
Val Gly Phe Leu Ser Gly Gly Val Asp Ser Cys Gln Gly Asp Ser Gly
            180                 185                 190
Gly Pro Leu Ser Ser Val Glu Ala Asp Gly Arg Ile Phe Gln Ala Gly
```

```
                 195                 200                 205
Val Val Ser Trp Gly Asp Gly Cys Ala Gln Arg Asn Lys Pro Gly Val
        210                 215                 220

Tyr Thr Arg Leu Pro Leu Phe Arg Asp Trp Ile Lys Glu Asn Thr Gly
225                 230                 235                 240

Val

<210> SEQ ID NO 3
<211> LENGTH: 366
<212> TYPE: DNA
<213> ORGANISM: Homo sapiens

<400> SEQUENCE: 3
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtagta gtggtgttaa cacacactac     180
gcagactccg tgaagggccg gttcaccatt tccagagaca attccaagaa cacgctgtat    240
ctgcaaatga acagcctgag agccgaggac acggccgtat attactgtgc gaccatcgct    300
agtatagcac ttcgggggta ctactttgac tactggggcc agggaaccct ggtcaccgtc    360
tcctca                                                                366

<210> SEQ ID NO 4
<211> LENGTH: 122
<212> TYPE: PRT
<213> ORGANISM: Homo sapiens

<400> SEQUENCE: 4

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Val Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Ile Ala Ser Ile Ala Leu Arg Gly Tyr Tyr Phe Asp Tyr Trp
            100                 105                 110

Gly Gln Gly Thr Leu Val Thr Val Ser Ser
        115                 120

<210> SEQ ID NO 5
<211> LENGTH: 324
<212> TYPE: DNA
<213> ORGANISM: Homo sapiens

<400> SEQUENCE: 5
gaaattgtgt tgacgcagtc tccaggcacc ctgtctttgt ctccagggga aagagccacc     60
ctctcctgca gggccagtca gactttggc agctcctatt tagcctggta ccagcagaaa    120
cctggccagg ctcccaggct cctcatctat ggtgcatcca gcagggccac tgtcatccca    180
gacaggttca gtggcagtgg gtctgggaca gacttcactc tcaccatcag cagactggag    240
```

```
cctgaagatt ttgcagtgta ttactgtcag cagtatggta gctcaccgtg acgttcggc      300 caagggacca aggtggaaat caaa                                             324
```

<210> SEQ ID NO 6
<211> LENGTH: 108
<212> TYPE: PRT
<213> ORGANISM: Homo sapiens

<400> SEQUENCE: 6

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Thr Phe Gly Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Val Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Pro
                 85                  90                  95

Trp Thr Phe Gly Gln Gly Thr Lys Val Glu Ile Lys
            100                 105
```

<210> SEQ ID NO 7
<211> LENGTH: 366
<212> TYPE: DNA
<213> ORGANISM: Homo sapiens

<400> SEQUENCE: 7

```
gaggtgcagc tgttggagtc tgggggaggc ttggtacagc ctggggggtc cctgagactc      60
tcctgtgcag cctctggagt cacctttagc agctatgcca tgagttgggt ccgccaggct     120
ccagggaagg gctggagtg gtctcagct attagtagta gtggtggtaa cacacactac       180
gcagactccg tgaagggccg gttcaccatc tccagagaca attccaagaa cacgctgtat     240
ctgcaaatga acagcctgag agccgaggac acggccgtat attactgtgc gaccatcgct     300
agtatagcga ctcgggggta cttctttaac tactggggcc agggaaccct ggtcaccgtc     360
tcctcg                                                                366
```

<210> SEQ ID NO 8
<211> LENGTH: 122
<212> TYPE: PRT
<213> ORGANISM: Homo sapiens

<400> SEQUENCE: 8

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Val Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Ser Gly Gly Asn Thr His Tyr Ala Asp Ser Val
     50                  55                  60

Lys Gly Arg Phe Thr Ile Ser Arg Asp Asn Ser Lys Asn Thr Leu Tyr
 65                  70                  75                  80
```

Leu Gln Met Asn Ser Leu Arg Ala Glu Asp Thr Ala Val Tyr Tyr Cys
                85                  90                  95

Ala Thr Ile Ala Ser Ile Ala Thr Arg Gly Tyr Phe Phe Asn Tyr Trp
            100                 105                 110

Gly Gln Gly Thr Leu Val Thr Val Ser Ser
        115                 120

<210> SEQ ID NO 9
<211> LENGTH: 324
<212> TYPE: DNA
<213> ORGANISM: Homo sapiens

<400> SEQUENCE: 9
gatattgtgt tgacgcagtc tccaggcacc ctgtctttgt ctccagggga aagagccacc      60
ctctcctgca gggccagtca gattttttagc agcaattcct tagcctggta ccagcagaaa    120
cctggccagg ctcccagcct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccgtg gacgttcggc    300
caagggacca aggtggaaat caaa                                           324

<210> SEQ ID NO 10
<211> LENGTH: 108
<212> TYPE: PRT
<213> ORGANISM: Homo sapiens

<400> SEQUENCE: 10

Asp Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ile Phe Ser Ser Asn
            20                  25                  30

Ser Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 11
<211> LENGTH: 109
<212> TYPE: PRT
<213> ORGANISM: Homo sapiens

<400> SEQUENCE: 11

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr

-continued

```
                65                  70                  75                  80
Leu Gln Met Asn Ser Leu Arg Ala Glu Asp Thr Ala Val Tyr Tyr Cys
                    85                  90                  95

Ala Lys Trp Gly Gln Gly Thr Leu Val Thr Val Ser Ser
            100                 105

<210> SEQ ID NO 12
<211> LENGTH: 99
<212> TYPE: PRT
<213> ORGANISM: Homo sapiens

<400> SEQUENCE: 12

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                 70                  75                  80

Pro Glu Asp Phe Ala Val Tyr Tyr Cys Phe Gly Gln Gly Thr Lys Val
                85                  90                  95

Glu Ile Lys
```

BINDING PROTEINS SPECIFIC FOR HUMAN MATRIPTASE

RELATED APPLICATIONS

This application claims priority to U.S. Provisional Application No. 60/637,859 filed on Dec. 20, 2004 and U.S. Provisional Application No. 60/706,467 filed on Aug. 8, 2005, each of which are hereby incorporated by reference in their entirety.

BACKGROUND OF THE INVENTION

1. Field of the Invention

The present invention relates to binding proteins, such as monoclonal antibodies, directed to the antigen Matriptase and uses of such binding proteins. More specifically, the present invention relates to fully human, high affinity neutralizing monoclonal antibodies directed to the antigen Matriptase and uses of these antibodies. Aspects of the invention also relate to cell lines expressing such antibodies. The antibodies herein are useful as diagnostics and as treatments for diseases associated with the activity and/or overproduction of Matriptase.

2. Description of the Related Art

Cancer metastasis involves a complex stepwise process involving cell to extracellular matrix communication, tumor cell attachment, spreading, migration, and the dissolution of tissue barriers. Several types of proteases appear to be expressed at elevated levels during cancer progression. The protease Matriptase is thought to be involved in the degradation of extracellular matrix (ECM) and in tissue remodeling, both of which are components of cancer progression and metastasis processes. Matriptase is also known as "MT-SP1" and Tumor-Associated differentially expressed Gene-15.

Matriptase is a transmembrane protein with a trypsin-like, extracellular serine protease domain. Human Matriptase (SEQ ID NO: 1) was initially isolated from human breast cancer cells. The Matriptase protein contains two tandem complement subcomponent "CUB" repeats (Complement factor/1R-urchin embryonic growth factor/bone morphogenic protein) and four tandem repeats of the low density lipoprotein receptor class "A" domain ("LDL"; Lin et al., J. Biol. Chem. 274: 18231-6 (1999)).

Matriptase primarily cleaves target proteins at arginine and lysine residues, similar to the majority of serine proteases, including trypsin and plasmin. Matriptase exhibits broad spectrum substrate cleavage activity which may contribute to its gelatinolytic activity. Several cancer-related proteins have been shown to be cleaved and activated by Matriptase. Among these are the protease activated receptor-2, urokinase-type plasminogen activator (Toshihiko et al., 2000, Journal of Biological Chemistry, 275:26333-26342); and hepatocyte growth factor (Lee et al., (2000), Journal of Biological Chemistry, 275:36720-36725).

The finding that Matriptase is involved in cancer progression has led researchers to investigate molecules that inhibit Matriptase activity. For example, U.S. Pat. No. 6,677,377 discusses small molecules which inhibit Matriptase, and their use in treating carcinoma progression. However, small molecule inhibitors can be non-specific for enzymes other than Matriptase, and may lead to undesirable toxicity following treatment.

Antibodies to Matriptase (MT-SP1) were discussed in Sun et al., 2003, Biochemistry 42: 892-900, and Lin et al., 1997, Journal of Biological Chemistry, 272: 9147-9152. However, because these antibodies were generated using phage display technology, they are potentially immunogenic in humans.

SUMMARY OF THE INVENTION

Embodiments of the invention relate to targeted binding agents directed to the antigen Matriptase. Particularly, embodiments of the invention relate to fully human monoclonal antibodies directed to Matriptase. Some antibodies described herein are advantageous in that they provide a higher affinity towards Matriptase, in addition to a higher potency, than previously described anti-Matriptase antibodies. Further, unlike antibodies prepared by other means, embodiments of the invention include antibodies that have a very low, or non-measurable, immunogenicity in humans.

One embodiment of the invention is a fully human antibody that specifically binds to Matriptase. The antibody may have a heavy chain amino acid sequence having complementarity determining regions (CDRs) contained within the sequences chosen from SEQ ID NO: 4 or 8. It is noted that CDR determinations can be readily accomplished by those of ordinary skill in the art. See for example, Kabat et al., *Sequences of Proteins of Immunological Interest*, Fifth Edition, NIH Publication 91-3242, Bethesda Md. [1991], vols. 1-3.

Yet another embodiment is an antibody that binds to Matriptase and comprises a light chain amino acid sequence having CDRs contained within the sequences chosen from SEQ ID NO: 6 or 10. In certain embodiments the antibody is a fully human monoclonal antibody. Embodiments of the invention also include fully human monoclonal antibodies that bind to the same Matriptase epitope as any of the antibodies described herein. Another embodiment of the invention is a fully human antibody that binds Matriptase and is capable of inhibiting cell migration in vitro or in vivo. Yet another embodiment is a fully human monoclonal antibody that binds to Matriptase, but does not result in a human anti-human antibody (HAHA) response when administered to a patient.

A further embodiment is an antibody that binds to Matriptase and comprises a heavy chain amino acid sequence comprising one of the sequences chosen from SEQ ID NO: 4 or 8 and a light chain amino acid sequence comprising one of the sequences chosen from SEQ ID NO: 6 or 10. In certain embodiments the antibody is a fully human monoclonal antibody. One of skill in the art will appreciate that sequences that are not identical to these sequences, but can be, for example, at least 85%, 90%, 95%, 98%, or 99% identical to SEQ ID NOs: 4, 6, 8, or 10, while still being embodiments of the invention.

Additional embodiments of the invention provide a nucleotide sequence encoding a heavy chain of an antibody that binds to Matriptase, comprising a nucleic acid sequence chosen from SEQ ID NO: 3 or 7. Further embodiments of the invention provide a nucleotide sequence encoding a light chain of an antibody that binds to Matriptase, comprising a nucleic acid sequence chosen from SEQ ID NO: 5 or 9.

In other embodiments the invention provides compositions, including an antibody or functional fragment thereof, and a pharmaceutically acceptable carrier. Also, embodiments of the invention include mixtures of fully human Matriptase antibodies and their use as therapeutic agents for the treatment of Matriptase related diseases.

Still further embodiments of the invention include methods of effectively treating an animal suffering from a neoplastic disease, including selecting an animal in need of treatment for such disease, and administering to said animal a therapeutically effective dose of a fully human monoclonal antibody that specifically binds to Matriptase.

Examples of neoplastic diseases that are treatable with antibodies directed against Matriptase include melanoma, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, lymphoma including Burkitt's lymphoma, Non-Hodgkins lymphoma, B-cell lymphoma, T-cell lymphoma and leukemia.

Further embodiments of the invention include the use of an antibody in the preparation of medicament for the treatment of a neoplastic disease in an animal, wherein said monoclonal antibody specifically binds to Matriptase.

Embodiments of the invention described herein relate to monoclonal antibodies that bind Matriptase and affect Matriptase function. Other embodiments relate to fully human anti-Matriptase antibodies and anti-Matriptase antibody preparations with desirable properties from a therapeutic perspective, including strong binding affinity for Matriptase, as well as the ability to neutralize Matriptase activity in vitro and in vivo.

In a preferred embodiment, antibodies described herein bind to Matriptase with very high affinities (Kd). For example a human, rabbit, mouse, chimeric or humanized antibody that is capable of binding Matriptase with a Kd less than, but not limited to, $10^{-5}$, $10^{-6}$, $10^{-7}$, $10^{-8}$, $10^{-9}$, $10^{-10}$, $10^{-11}$, $10^{-12}$, $10^{-13}$ or $10^{-14}$ M, or any range or value therein. Affinity and/or avidity measurements can be measured by KinExA® and/or BIACORE®, as described herein. Additional embodiments of the invention provide a fully human monoclonal antibody that binds to Matriptase with a $K_D$ of less than 80 pM, 60 pM, 50 pM, 40 pM, 30 pM, or 25 pM. One embodiment is a fully human monoclonal antibody that binds to Matriptase with a $K_D$ of less than 50 pM. Another embodiment is a fully human monoclonal antibody that binds to Matriptase with a $K_D$ of less than 20 pM.

Additional embodiments of the invention provide a fully human monoclonal antibody that has a Ki for Matriptase of less than about 100, 80, 70, 60, 50, 40, 30, 20, 18, or 10 pM. One embodiment is a fully human monoclonal that has a Ki for Matriptase of less than about 15 pM.

Accordingly, one embodiment described herein includes isolated antibodies, or fragments of those antibodies, that bind to Matriptase. Embodiments of the invention described herein also provide cells for producing these antibodies.

It will be appreciated that embodiments of the invention are not limited to any particular form of an antibody or method of generation or production. For example, the anti-Matriptase antibody may be a full-length antibody (e.g., having an intact human Fc region) or an antibody fragment (e.g., a Fab, Fab' or $F(ab')_2$). In addition, the antibody may be manufactured from a hybridoma that secretes the antibody, or from a recombinantly produced cell that has been transformed or transfected with a gene or genes encoding the antibody.

Other embodiments of the invention include isolated nucleic acid molecules encoding any of the antibodies described herein, vectors having isolated nucleic acid molecules encoding anti-Matriptase antibodies or a host cell transformed with any of such nucleic acid molecules. In addition, one embodiment of the invention is a method of producing an anti-Matriptase antibody by culturing host cells under conditions wherein a nucleic acid molecule is expressed to produce the antibody followed by recovering the antibody.

A further embodiment herein includes a method of producing high affinity antibodies to Matriptase by immunizing a mammal with human Matriptase, or a fragment thereof.

Another embodiment of the invention includes a method of diagnosing diseases or conditions in which an antibody prepared as described herein is utilized to detect the level of Matriptase in a biological sample from a patient. In one embodiment, the patient sample is tissue from the liver, breast, skin, prostate, ovary, bladder, kidney, colon, lymph node, lymphatic system or pancreas. In further embodiments, methods for the identification of risk factors, diagnosis of disease, and staging of disease is presented which involves the identification of the overexpression of Matriptase using anti-Matriptase antibodies.

In another embodiment, the invention includes an assay kit for detecting Matriptase and Matriptase family members in mammalian tissues or cells to screen for neoplastic diseases. The kit includes an antibody that binds to Matriptase and a means for indicating the reaction of the antibody with Matriptase, if present. Preferably the antibody is a monoclonal antibody. In one embodiment, the antibody that binds Matriptase is labeled. In another embodiment the antibody is an unlabeled primary antibody and the kit further includes a means for detecting the primary antibody. In one embodiment, the means includes a labeled second antibody that is an anti-immunoglobulin. Preferably the antibody is labeled with a marker selected from the group consisting of a fluorochrome, an enzyme, a radionuclide and a radiopaque material.

Other embodiments of the invention include pharmaceutical compositions having an effective amount of an anti-Matriptase antibody in admixture with a pharmaceutically acceptable carrier or diluent. In yet other embodiments, the anti-Matriptase antibody, or a fragment thereof, is conjugated to a therapeutic agent. The therapeutic agent can be, for example, a toxin or a radioisotope.

Yet another embodiment includes methods for treating diseases or conditions associated with the expression of Matriptase in a patient, by administering to the patient an effective amount of an anti-Matriptase antibody. The anti-Matriptase antibody can be administered alone, or can be administered in combination with additional antibodies. For example, an oligoclonal or polyclonal mixture of Matriptase antibodies can be administered. The method can be performed in vivo. The patient is preferably a human patient.

In another embodiment, the invention provides an article of manufacture including a container. The container includes a composition containing an anti-Matriptase antibody, and a package insert or label indicating that the composition can be used to treat diseases characterized by the overexpression of Matriptase.

In some embodiments, the anti-Matriptase antibody is administered to a patient, followed by administration of a clearing agent to remove excess circulating antibody from the blood.

In some embodiments, anti-Matriptase antibodies can be modified to enhance their capability of fixing complement and participating in complement-dependent cytotoxicity (CDC). In one embodiment, anti-Matriptase antibodies can be modified, such as by an amino acid substitution or their state of glycosylation, to alter their clearance from the body.

Alternatively, some other amino acid substitutions may slow clearance of the antibody from the body.

DETAILED DESCRIPTION OF THE PREFERRED EMBODIMENT

Figure 1A:
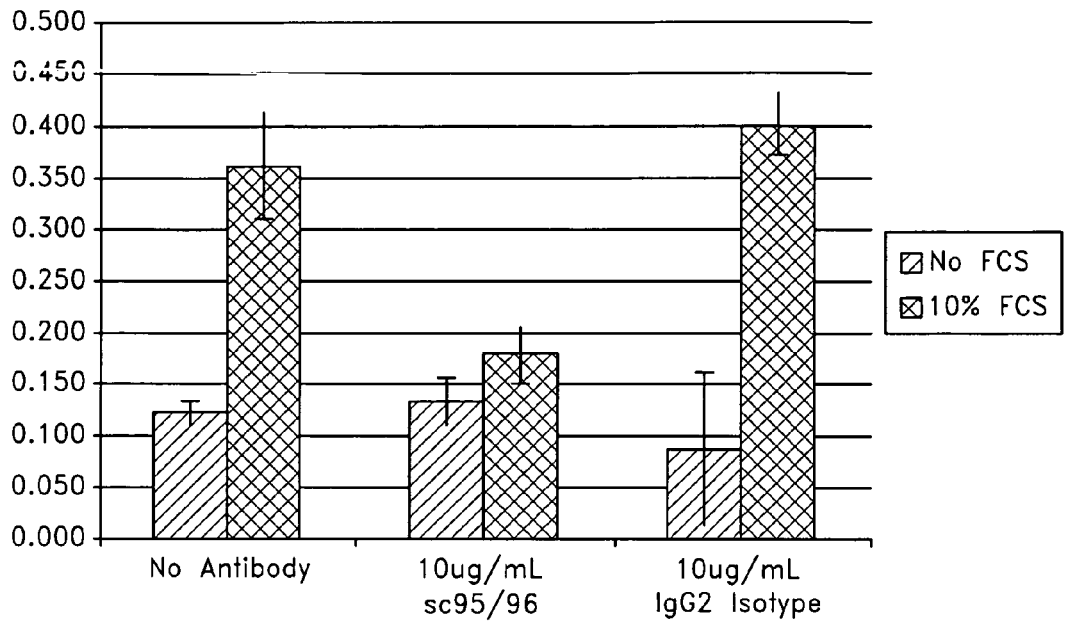
FIGS. 1A and 1B are bar graphs showing the results of an inhibition of migration assay, as described in Example 15, using 22Rv1 cells (FIG. 1A) and JEG-3 cells (FIG. 1B). The bars represent measurements without FCS or in the presence of 10% FCS.

Embodiments of the invention relate to targeted binding agents that specifically bind to Matriptase. In one embodiment, the targeted binding agents are antibodies. In another embodiment, the targeted binding agents are fully human anti-Matriptase antibodies, antibody fragments, or antibody preparations, with desirable properties from a therapeutic perspective. Desirable properties include strong binding affinity for Matriptase and the ability to neutralize Matriptase in vivo. Such neutralization can prevent or reduce the level of neoplastic disease in a patient. In one embodiment, the antibodies do not raise a human anti-human antibody (HAHA) response when administered to a patient.

Embodiments of the invention also include antibodies that bind to the same Matriptase epitope and compete with the antibodies described herein. Also within the scope of the invention are isolated fragments of anti-Matriptase antibodies and cells, such as hybridomas, for producing these antibodies.

In addition, embodiments of the invention include methods for using these antibodies as a diagnostic tool or for treatment of a disease. For example, one embodiment of the invention includes methods for inhibiting binding of Matriptase to its target substrates. Preferably, the antibodies are used to treat neoplastic diseases, including, but not limited to, melanoma, non-small cell lung cancer, glioma, hepatocellular (liver) carcinoma, glioblastoma, lymphoma including Burkitt's lymphoma, Non-Hodgkins lymphoma, B-cell lymphoma, T-cell lymphoma, leukemia and cancers and tumors of the thyroid, stomach, prostate, breast, ovary, bladder, lung, uterus, kidney, colon, pancreas, lymph node, lymphatic system and salivary gland. Because Matriptase is widely expressed on all epithelial cells, the anti-Matriptase antibodies discussed herein can be a useful therapeutic for all types of epithelial cancers.

Another embodiment of the invention is an article of manufacture that includes antibodies against Matriptase. Another embodiment includes an assay kit having antibodies as described herein to screen for neoplastic diseases in patients.

Additionally, the nucleic acids described herein, and fragments and variants thereof, may be used, by way of non-limiting example, (a) to encode the corresponding proteins, polypeptides, fragments and variants as recombinant or heterologous gene products, (b) as probes for detection and quantification of the nucleic acids disclosed herein, (c) as sequence templates for preparing antisense molecules, (d) as sequence templates for the preparation of oligopeptides binding to Matriptase, and the like. Such uses are described more fully in the following disclosure.

Furthermore, the Matriptase proteins and polypeptides described herein, and fragments and variants thereof, may be used in ways that include (a) serving as an immunogen to stimulate the production of an anti-Matriptase antibody, (b) a capture antigen in an immunogenic assay for such an antibody, (c) as a target for screening for substances that bind to a Matriptase polypeptide described herein, and (d) a target for a Matriptase specific antibody such that treatment with the antibody affects the molecular and/or cellular function mediated by the target.

Another embodiment of the invention includes a method of diagnosing diseases or conditions in which an antibody prepared as described herein is utilized to detect the level of Matriptase in a biological sample from a patient. In one embodiment, the patient sample is tissue from the liver, breast, skin, prostate, ovary, bladder, kidney, colon, lymph node, lymphatic system or pancreas. In further embodiments, methods for the identification of risk factors, diagnosis of disease, and staging of disease is presented which involves the identification of the overexpression of Matriptase using anti-Matriptase antibodies.

Further embodiments, features, and the like regarding the anti-Matriptase antibodies are provided in additional detail below.

Sequence Listing

Embodiments of the invention include the specific anti-Matriptase antibodies listed below in Table 1. This table reports the identification number of each anti-Matriptase antibody, along with the SEQ ID number of the corresponding heavy chain and light chain genes. The variable heavy chains and the variable light chains of the antibodies were sequenced to determine their DNA sequences. The heavy chain and light chain variable region nucleotide and amino acid sequences of representative human anti-Matriptase antibodies are provided in the sequence listing.

TABLE 1

| mAb ID No.: | Sequence | SEQ ID NO: |
|---|---|---|
| sc95/96 | Nucleotide sequence encoding the variable region of the heavy chain | 3 |
| | Amino acid sequence encoding the variable region of the heavy chain | 4 |
| | Nucleotide sequence encoding the variable region of the light chain | 5 |
| | Amino acid sequence encoding the variable region of the light chain | 6 |
| sc136 | Nucleotide sequence encoding the variable region of the heavy chain | 7 |
| | Amino acid sequence encoding the variable region of the heavy chain | 8 |
| | Nucleotide sequence encoding the variable region of the light chain | 9 |
| | Amino acid sequence encoding the variable region of the light chain | 10 |

Definitions

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "MT-SP1" refers to the molecule Matriptase.

The term "neutralizing" when referring to an antibody relates to an antibody's ability to eliminate or significantly reduce the activity of a target antigen to which is binds. Accordingly, a "neutralizing" anti-Matriptase antibody is capable of eliminating or significantly reducing the activity of Matriptase. A neutralizing Matriptase antibody may, for example, act by blocking the binding of Matriptase to its substrates, hence, blocking the enzymatic activity of Matriptase.

The term "isolated polynucleotide" as used herein shall mean a polynucleotide of genomic, cDNA, or synthetic origin or some combination thereof, which has been isolated from its natural environment. An "isolated polynucleotide" typically (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of genomic DNA, cDNA, recombinant DNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "control sequence" as used herein refers to polynucleotide sequences that are necessary either to effect or to affect the expression and processing of coding sequences to which they are connected. The nature of such control sequences differs depending upon the host organism; in prokaryotes, such control sequences generally include promoter, ribosomal binding site, and transcription termination sequence; in eukaryotes, generally, such control sequences may include promoters, introns and transcription termination sequence. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

The term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison. A reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least about 18 contiguous nucleotide positions or about 6 amino acids wherein the polynucleotide sequence or amino acid sequence is compared to a reference sequence of at least 18 contiguous nucleotides or 6 amino acid sequences and wherein the portion of the polynucleotide sequence in the comparison window may include additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad Sci. (U.S.A.)* 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), GENEWORKS™, or MACVECTOR® software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the antibodies described herein.

Preferred amino acid substitutions are those which: (1) reduce susceptibility to proteolysis, (2) reduce. susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); Introduction to Protein Structure (C. Branden and J. Tooze, eds., Garland Publishing, New York, N.Y. (1991)); and Thornton et at. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to Matriptase under suitable binding conditions, (2) ability to block appropriate Matriptase binding, or (3) ability to inhibit Matriptase activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p.392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

As used herein, the term "antibody" refers to an immunoglobulin polypeptide or group of polypeptides which form at least one binding domain that is specific for an antigenic determinant on a target molecule.

As used herein, a "targeted binding agent" is an antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope on Matriptase.

"Specifically binds" refers to the ability of individual antibodies to specifically immunoreact with an antigen. The binding is a non-random binding reaction between an antibody molecule and an antigenic determinant of the target cytokine or receptor. The desired binding specificity is typically determined from the reference point of the ability of the antibody to differentially and preferentially bind the target cytokine or receptor and an unrelated antigen, and therefore distinguish between two different antigens, particularly where the two antigens have unique epitopes. An antibody that specifically binds to a particular epitope is referred to as a "specific antibody".

Binding fragments are produced by recombinant DNA techniques, or by enzymatic or chemical cleavage of intact antibodies. Binding fragments include Fab, Fab', $F(ab')_2$, Fv, and single-chain antibodies. An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

The term "epitope" includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is $\leq 1$ µM, preferably $\leq 100$ nM, more preferably $\leq 10$ nM, and most preferably $\leq 100$ pM.

The term "agent" is used herein to denote a chemical compound, a mixture of chemical compounds, a biological macromolecule, or an extract made from biological materials.

"Active" or "activity" in regard to a Matriptase polypeptide refers to a portion of a Matriptase polypeptide that has a biological or an immunological activity of a native Matriptase polypeptide. "Biological" when used herein refers to a biological function that results from the activity of the native Matriptase polypeptide. A preferred Matriptase biological activity includes, for example, Matriptase-induced tumor progression.

"Mammal" when used herein refers to any animal that is considered a mammal. Preferably, the mammal is human.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a $F(ab')_2$ fragment in which the two arms of the antibody molecule remain linked and comprise two-antigen binding sites. The $F(ab')_2$ fragment has the ability to crosslink antigen.

"Fv" when used herein refers to the minimum fragment of an antibody that retains both antigen-recognition and antigen-binding sites.

"Fab" when used herein refers to a fragment of an antibody that comprises the constant domain of the light chain and the CH1 domain of the heavy chain.

The term "mAb" refers to monoclonal antibody.

"Liposome" when used herein refers to a small vesicle that may be useful for delivery of drugs that may include the Matriptase polypeptide of the invention or antibodies to such an Matriptase polypeptide to a mammal.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^3H$, $^{14}C$, $^{15}N$, $^{35}S$, $^{90}Y$, $^{99}Tc$, $^{111}In$, $^{125}I$, $^{131}I$, fluorescent labels may include rhodamine, lanthanide phosphors or FITC and enzymatic labels may include horseradish peroxidase, β-galactosidase, luciferase, alkaline phosphatase.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

The term "Matriptase expressing tissue" refers to any tissue which expresses any form of Matriptase, either malignant, pre-malignant, normal tissue, or tissue which is subject to another pathological condition.

The term "malignancy" refers to a tissue, cell or organ which contains a neoplasm or tumor that is cancerous as opposed to benign. Malignant cells typically involve growth that infiltrates tissue (e.g., metastases). By "benign" is meant an abnormal growth which does not spread by metastasis or infiltration of the tissue. The malignant cell can be of any tissue.

By "tumor progression" or "tumor metastasis" is meant the ability of a tumor to develop secondary tumors at a site remote from the primary tumor. Tumor metastasis typically requires local progression, passive transport, deposition and proliferation at a remote site. In some embodiments, the process also requires the development of tumor vascularization, a process termed angiogenesis. Therefore, the terms "tumor progression" and "metastasis," may also include the process of tumor angiogenesis.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function and extending circulating half-life through binding to FcRn. Human light chains are classified as kappa and lambda light chains. Heavy chains are classified as mu, delta, gamma, alpha, or epsilon, and define the antibody's isotype as IgM, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J. Immunol.* 148:1547-1553 (1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XENOMOUSE® strains of mice that have been engineered to contain 245 kb and 190 kb-sized germline configuration fragments of the human heavy chain locus and kappa light chain locus. See Mendez et al. *Nature Genetics* 15:146-156 (1997) and Green and Jakobovits *J. Exp. Med.* 188:483-495 (1998). The XENOMOUSE® strains of mice are available from Abgenix, Inc. (Fremont, Calif.).

The production of the XENOMOUSE® strains of mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031, 801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464, 582, filed Jun. 5, 1995, Ser. No. 08/463,191, filed Jun. 5, 1995, Ser. No. 08/462,837, filed Jun. 5, 1995, Ser. No. 08/486, 853, filed Jun. 5, 1995, Ser. No. 08/486,857, filed Jun. 5, 1995, Ser. No. 08/486,859, filed Jun. 5, 1995, Ser. No. 08/462, 513, filed Jun. 5, 1995, Ser. No. 08/724,752, filed Oct. 2, 1996, and 08/759,620, filed Dec. 3, 1996 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International patent application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B 1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Other groups have demonstrated the generation of human antibodies from "Tc" mice in which, through microcell fusion, large pieces of chromosomes, or entire chromosomes, have been introduced. See European Patent Application Nos. 773 288 and 843 961, the disclosures of which are hereby incorporated by reference. Additionally, KM™—mice, which are the result of cross-breeding of Tc mice with Medarex's minilocus (Humab) mice have been generated. These mice possess the HC transchromosome of the Tc mice and the kappa chain transgene of the Genpharm mice (Ishida et al., Cloning Stem Cells, (2002) 4:91-102).

Human antibodies can also be derived by in vitro methods. Suitable examples include, but are not limited to, phage display, ribosome display, yeast display, and the like.

Suitable antibodies can also be derived using well-known humanization technology. "Humanized" forms of non-human antibodies are chimeric immunoglobulins, immunoglobulin chains or fragments thereof (such as Fv, Fab, Fab', F(ab')2) which contain minimal sequences derived from non-human immunoglobulin. For the most part, humanized antibodies are human immunoglobulins in which residues from a complementary-determining region (CDR) are replaced by residues from a CDR of a non-human species having the desired specificity, affinity, and capacity. Furthermore, humanized antibodies can comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

The use of novel protein scaffolds may also be useful for generating antibodies against Matriptase. Although such structures are not formally antibodies, they can be designed to function in a somewhat similar manner.

Antibody Therapeutics

As discussed herein, the function of the Matriptase antibody appears important to at least a portion of its mode of operation. By function, is meant, by way of example, the activity of the Matriptase antibody in operation with Matriptase. There are a number of isotypes of antibodies that are capable of activity against Matriptase, including the following: murine IgM, murine IgG2a, murine IgG2b, murine IgG3, human IgM, human IgG1, human IgG2, human IgG3 and human IgG4. In humans, the isotypes IgM, IgA, IgG1 and IgG3 fix complement much more potently than do IgG4 and IgG2. It will be appreciated that antibodies that are generated need not initially possess such an isotype. The generated antibody can possess any isotype and then be isotype switched using conventional techniques that are well known in the art. Such techniques include the use of direct recombinant techniques (see e.g., U.S. Pat. No. 4,816,397), cell-cell fusion techniques (see e.g., U.S. Pat. Nos. 5,916,771 and 6,207,418), among others.

In the cell-cell fusion technique, a myeloma or other cell line is prepared that possesses a DNA construct capable of expressing the antibody heavy chain with any desired isotype and another myeloma or other cell line is prepared that possesses a DNA construct capable of expressing the antibody light chain. Such cells can, thereafter, be fused and a cell line expressing an intact antibody can be isolated.

By way of example, the Matriptase antibody discussed herein is a human anti-Matriptase IgG2 antibody. If such antibody possessed desired binding to the Matriptase molecule, it could be readily isotype switched to generate a human IgM, human IgA, human IgG1, human IgG3 or human IgG4 isotype, while still possessing the same variable region (which defines the antibody's specificity and some of its affinity).

Accordingly, as antibody candidates are generated that meet desired "structural" attributes as discussed above, they can generally be provided with at least certain of the desired "functional" attributes through isotype switching.

Design and Generation of Other Therapeutics

In accordance with the present invention and based on the activity of the antibodies that are produced and characterized herein with respect to Matriptase, the design of other therapeutic modalities beyond antibody moieties is facilitated. Such modalities include, without limitation, advanced antibody therapeutics, such as bispecific antibodies, immunotoxins, and radiolabeled therapeutics, single domain antibodies, generation of peptide therapeutics, Matriptase binding domains in novel scaffolds, gene therapies, particularly intrabodies, antisense therapeutics, and small molecules.

In connection with the generation of advanced antibody therapeutics, where complement fixation is a desirable attribute, it may be possible to sidestep the dependence on complement for cell killing through the use of bispecific antibodies, immunotoxins, or radiolabels, for example.

Bispecific antibodies can be generated that comprise (i) two antibodies one with a specificity to Matriptase and another to a second molecule that are conjugated together, (ii)

a single antibody that has one chain specific to Matriptase and a second chain specific to a second molecule, or (iii) a single chain antibody that has specificity to Matriptase and the other molecule. Such bispecific antibodies can be generated using techniques that are well known; for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer (Suppl.)* 7:51-52 (1992). In each case, the second specificity can be made to the heavy chain activation receptors, including, without limitation, CD16 or CD64 (see e.g., Deo et al. *Immunol. Today* 18:127 (1997)) or CD89 (see e.g., Valerius et al. *Blood* 90:4485-4492 (1997)).

In connection with immunotoxins, antibodies can be modified to act as immunotoxins utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902.

Preparation of Anti-Matriptase Antibodies

As will be appreciated, anti-Matriptase antibodies can be expressed in a variety of cell lines including hybridomas and recombinant cells. To make recombinant cell lines expressing anti-Matriptase antibodies, sequences encoding particular antibodies can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive Matriptase binding properties.

Therapeutic Administration and Formulations

Biologically active anti-Matriptase antibodies as described herein may be used in a sterile pharmaceutical preparation or formulation to inhibit the binding of Matriptase to its substrates. Anti-Matriptase antibodies preferably possess adequate affinity to potently neutralize Matriptase, and preferably have an adequate duration of action to allow for infrequent dosing. A prolonged duration of action will allow for less frequent and more convenient dosing schedules by alternate parenteral routes such as subcutaneous or intramuscular injection.

When used for in vivo administration, the anti-Matriptase antibody formulation is preferably sterile. This is readily accomplished, for example, by filtration through sterile filtration membranes, prior to or following lyophilization and reconstitution. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

An effective amount of anti-Matriptase antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Anti-Matriptase antibodies, as described herein, can be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington: The Science and Practice of Pharmacy* ($20^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired.

Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(-)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulthydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitoneally can produce a sustained release effect. Other compositions also include liposomally entrapped antibodies. Liposomes containing such antibodies are prepared by methods known per se: U.S. Pat. No. DE 3,218,121; Epstein et al., *Proc. Natl. Acad. Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544, 545; and EP 102,324.

The dosage of the anti-Matriptase antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the anti-Matriptase antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.001 mg/kg to up to 100 mg/kg or more, depending on the factors mentioned above. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationie or anionic) containing vesicles (such as LIPOFBCTIN™ transfection reagent), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicot. Pharmacol* 32(2):210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J Pharm Sci.* 89(8):967-78 (2000), Powell a at "Compendium of excipients for parenteral formulations" *PDA J Pharni Sd Technol.* 52:238-311 (1998) and the citations therein for additional information related to formulations, excipients and carriers well known to pharmaceutical chemists.

EXAMPLES

The following examples, including the experiments conducted and results achieved are provided for illustrative purposes only and are not to be construed as limiting upon the teachings herein.

Example 1

Immunization with Matriptase

Soluble protein containing the Matriptase catalytic domain (SEQ ID NO: 2), which corresponds to amino acids 615-855 of the Matriptase protein (SEQ ID NO: 1) was used as the antigen. XENOMOUSE® strains of animals (XENOMOUSE® strain XMG2/kappa, Abgenix, Inc. Fremont, Calif.) were immunized 10 times before harvest. The first six immunizations were performed using CpG/Alum as the adjuvant, and the site of immunization alternated between intraperitoneal cavity (IP) and base of tail (BoT). After six immunizations, the animals were titered to assess the immune response to the antigen. To improve the titers, four addition boosts were performed. The $7^{th}$ immunization and the $9^{th}$ immunization were performed using TiterMax Gold (CytRx Corporation, Noreross, Ga.) as the adjuvant (IP); the $8^{th}$ immunization was performed using CpG/Alum as the adjuvant (BoT) and the $10^{th}$ minimization was performed in PBS (BoT). The immunizations were administered on day 0, 4, 8, 11, 15, 18, 22, 25, 28 and 31. The animals were harvested on day 35 to isolate antigen-specific B cells. This harvesting and initial selection process is described below.

Example 2

Selection of Animals for Harvest

Antigen-specific antibody titers for each of the XenoMice were determined by ELISA. ELISA plates were prepared by coating Streptavidin-labeled 96-well plates (Corning, Acton, Mass.) with the biotinylated catalytic domain of Matriptase.

The following method was used to prepare the biotinylated antigen. The catalytic domain of Matriptase (150 µg) was buffer changed into 50 mM sodium bicarbonate pH 8.5 by washing three times in a 5 kDa spin column. The protein was brought up to 1 mL in 50 mM sodium bicarbonate pH 8.5 containing 120 µpg of Biotin-X-NHS (biotinamidocaproate N-hydroxysuccinimide ester) and allowed to rotate for 1 hour at room temperature. The reaction was stopped by washing the sample three times in a buffer containing 150 mM sodium chloride and 50 mM HEPES, pH 6.5 in a 5 kDa spin column. After washing, the biotinylated protein sample was resuspended at a concentration of 300 µg/mL in the buffer described above.

The solution containing unbound antigen was removed and the plates were washed five times with $dH_2O$. Sera from the immunized XENOMOUSE® strains of animals, or naive XENOMOUSE® strains of animals, were titrated in 2% milk/PBS at 1:2 dilutions in duplicate from a 1:100 initial dilution. The last well was left blank. The plates were washed five times with $dH_2O$. A goat anti-human IgG Fc-specific horseradish peroxidase (HRP, Pierce, Rockford, Ill.) conjugated antibody was added at a final concentration of 1 µg/mL for 1 hour at room temperature. The plates were washed five times with $dH_2O$. The plates were developed with the addition of TMB chromogenic substrate (BioFx BSTP-0100-01; Gaithersburg, Md.) for 30 minutes and the ELISA was stopped by the addition of 1 M phosphoric acid.

The specific titer of individual XENOMOUSE® strains of animals was determined from the optical density at 450 aim. The titer represented the reciprocal dilution of the serum required to give 50% of maximal signal. Therefore, the higher the number, the greater the humoral immune response to the antigen. The animals 486-2 and 486-3 were selected for harvest based on the titer data shown in Table 2, below.

TABLE 2

| Mouse | Titer |
|---|---|
| 486-1 | 1083 |
| 486-2 | 20727 |
| 486-3 | 12497 |
| 488-1 | 3978 |
| 488-2 | 7692 |
| 488-3 | 1406 |
| 488-4 | 6237 |
| 488-5 | 1192 |
| naïve | <100 @ 1.458 |

Example 3

Preparation and Screening of B Cell Cultures

Culture of B cells. $CD19^+/CD138^-$ B cells were isolated from the draining lymph nodes of the hyperimmune animals. The cells were cultured to allow them to proliferate and terminally differentiate into antibody-secreting plasma cells. Forty 96-well culture plates were set-up at 50 and 150 $CD19^+/CD138^-$ B cells per well.

Screening of the B cell culture supernatants. The supernatants from the B cell cultures were analyzed for the presence of antigen-specific antibody using ELISA. ELISA was performed as described above in Example 2 on every well in order to identify wells having antigen-specific antibodies. This led to the identification of 972 wells with optical densities above background levels. These supernatants were selected for further analysis.

All 972 wells were then analyzed in an enzymatic assay using the catalytic domain of Matriptase and the tripeptide QAR-MCA (Peptides International Inc., Louisville, Ky.) as substrate. The cleavage of the QAR-MCA substrate by Matriptase causes the release of a methylcoumarin amide group (MCA) as amino-methyl coumarin (AMC). The free AMC can then be detected using a fluorescent reader as a measure of Matriptase activity.

The development of the assay method was complicated by the finding that an unknown protease was present in the B cell culture supernatant that was able to cleave the QAR-MCA substrate. However, adding the small molecule inhibitor phenylmethyl sulfonyl fluoride (PMSF) was found to be useful for preventing the activity of the unknown protease. PMSF could be used at a concentration that would completely inhibit the activity of the unknown protease without affecting the activity of Matriptase. This was advantageous as the background cleavage would no longer affect the ability to identify neutralizing antibodies against Matriptase. The supernatant also contained an unknown Matriptase inhibitor that necessitated a relatively high Matriptase concentration in the assay.

The data from the top six neutralizing wells is shown below in Table 3. The wells were determined to be positive based on their ability to inhibit Matriptase activity in two assays compared with average of the irrelevant control wells (enzyme, substrate and B cell culture supernatant) shown below. The data is shown as a percentage of the average of the negative control wells (enzyme and substrate) as in Table 3.

TABLE 3

| Screening Results | | | | | |
|---|---|---|---|---|---|
| Well ID | | ELISA | Tripeptide - MCA Assay | | |
| Plate | Well | OD | Assay 1 | Assay 2 | Comments |
| 298 | F7 | 4.786 | 20% | 23% | Strong inhibitor |
| 351 | D2 | 1.308 | 39% | 46% | Strong inhibitor |
| 342 | A7 | 2.815 | 42% | 48% | Strong inhibitor |
| 322 | B4 | 0.918 | 74% | 79% | Inhibitor |
| 321 | E8 | 1.601 | 90% | 99% | Weak inhibitor |
| 345 | G10 | 1.154 | 95% | 104% | Weak inhibitor |
| Irrelevant Control Wells | | | 130% | 139% | |
| Negative Control Wells | | | 100% | 100% | |

Example 4

Matriptase-specific Hemolytic Plague Assay

A Matriptase-specific hemolytic plaque assay was then performed in order to screen for antibody-producing cells secreting antibodies to Matriptase. The preparation of a number of specialized reagents and materials needed to conduct the assay are described below.

Biotinylation of Sheep red blood cells (SRBC). SRBC were stored in RPMI media as a 25% stock. A 250 µl SRBC packed-cell pellet was obtained by aliquoting 1.0 mL of the stock into a 15-mL falcon tube, spinning down the cells and removing the supernatant. The cell pellet was then re-suspended in 4.75 mL PBS at pH 8.6 in a 50 mL tube. In a separate 50 mL tube, 2.5 mg of Sulfo-NHS biotin was added to 45 mL of PBS at pH 8.6. Once the biotin had completely dissolved, 5 mL of SRBCs was added and the tube was rotated at room temperature for 1 hour. The SRBCs were centrifuged at 3000 g for 5 minutes. The supernatant was drawn off and 25 mL PBS at pH 7.4 was added as a wash. The wash cycle was repeated 3 times, then 4.75 mL immune cell media (RPMI 1640 with 10% FCS) was added to the 250 µl biotinylated-SRBC (B-SRBC) pellet to gently re-suspend the B-SRBC (5% B-SRBC stock). The stock was stored at 4° C. until needed.

Streptavidin (SA) coating of B-SRBC. One mL of the 5% B-SRBC stock was transferred into to a fresh eppendorf tube. The B-SRBC cells were pelleted with a pulse spin at 8000 rpm (6800 rcf) in a microfuge. The supernatant was then drawn off, the pellet was re-suspended in 1.0 mL PBS at pH 7.4, and the centrifugation was repeated. The wash cycle was repeated 2 times, then the B-SRBC pellet was resuspended in 1.0 mL of PBS at pH 7.4 to give a final concentration of 5% (v/v). 10 µl of a 10 mg/mL Streptavidin (CalBiochem, San Diego, Calif.) stock solution was added. The tube was mixed and rotated at RT for 20 minutes. The washing steps were repeated and the SA-SRBC were re-suspended in 1 mL PBS pH 7.4 (5% (v/v)).

Human Matriptase coating of SA-SRBC. The SA-SRBC were coated with the biotinylated-catalytic domain of Matriptase at 50 µg/mL, mixed and rotated at room temperature for 20 minutes. The SRBC were washed twice with 1.0 mL of PBS at pH 7.4 as above. The Ag-coated SRBC were re-suspended in RPMI (+10%FCS) to a final concentration of 5% (v/v).

Determination of the quality of Matriptase-SRBC by immunofluorescence (IF). 10 µl of 5% SA-SRBC and 10 µl of 5% Ag-coated SRBC were each added to separate fresh 1.5 mL eppendorf tube containing 40 µl of PBS. Human anti-Matriptase antibodies were added to each sample of SRBCs at 50 µg/mL. The tubes were rotated at room temperature for 25 min, and the cells were then washed three times with 100 µl of PBS. The cells were re-suspended in 50 µl of PBS and incubated with 2 µg/mL Gt-anti Human IgG Fc antibody conjugated to the photostable fluorescent dye Alexa488 (Molecular Probes, Eugene, Oreg.). The tubes were rotated at room temperature for 25 min, followed by washing with 100 pl PBS and re-suspension in 10 µl PBS. 10 µl of the stained cells were spotted onto a clean glass microscope slide, covered with a glass coverslip, observed under fluorescent light, and scored on an arbitrary scale of 0-4 to assess the quality of the isolated cells.

Preparation of plasma cells. The contents of a single B cell culture well previously identified as neutralizing for Matriptase activity (therefore containing a B cell clone secreting the immunoglobulin of interest), was harvested. The B cell culture present in the well was recovered by addition of RPMI +10% FCS at 37° C. The cells were resuspended by pipetting and then transferred to a fresh 1.5 mL eppendorf tube (final volume approximately 500-700 µl). The cells were centrifuged in a microfuge at 1500 rpm (240 rcf) for 2 minutes at room temperature, then the tube was rotated 180 degrees and centrifuged again for 2 minutes at 1500 rpm. The freeze media was drawn off and the immune cells were resuspended in 100 µl RPMI (10% FCS), then centrifuged. This washing with RPMI (10% FCS) was repeated and the cells re-suspended in 60 µl RPMI (FCS) and stored on ice until ready to use.

Performance of the Hemolytic Plaque Assay. To the 60 µl sample of immune cells was added 60 µl each of Matriptase-coated SRBC (5% v/v stock), 4× guinea pig complement (Sigma, Oakville, ON) stock prepared in RPMI (FCS), and 4× enhancing sera stock (1:900 in RPMI (FCS)). The mixture (3-5 µl) was spotted onto plastic lids from 100 mm Falcon tissue culture plates and the spots were covered with undiluted paraffin oil. The slides were incubated at 37° C. for a minimum of 45 minutes.

Analysis of Plaque assay results. The coating of the sheep red blood cells with the catalytic domain of human Matriptase was successful. The control antibodies yielded fluorescent signals of 1.5-2/4 on Ag-coated SRBC and signals of 0/4 on SA-coated SRBC. These Ag-coated red blood cells were then used to identify antigen-specific plasma cells from the wells shown below in Table 4. For example, the analysis of well 298F7 led to the identification of 20 plasma cells (sc-135-154) encoding an antibody against Matriptase. These cells were then isolated by micromanipulation. After micromanipulation to rescue the antigen-specific plasma cells, the genes encoding the variable region genes were rescued by RT-PCR on a single plasma cell.

TABLE 4

Plaque Assay Results

| Well ID | | ELISA | Tripeptide - MCA Assay | | Single Cell |
|---|---|---|---|---|---|
| Plate | Well | OD | Assay 1 | Assay 2 | (sc) Numbers |
| 298 | F7 | 4.786 | 20% | 23% | sc-135-154 |
| 351 | D2 | 1.308 | 39% | 46% | sc115-134 |
| 342 | A7 | 2.815 | 42% | 48% | sc-95-114 |
| 322 | B4 | 0.918 | 74% | 79% | sc-37-56 |
| 321 | E8 | 1.601 | 90% | 99% | sc57-76 |
| 345 | G10 | 1.154 | 95% | 104% | sc77-94 |

Example 5

Cloning and Expression of Anti-Matriptase Antibodies

After isolation of the desired single plasma cells from Example 4, mRNA was extracted and reverse transcriptase PCR was conducted to generate cDNA with antisense primers specific for the mRNA of interest. The resulting cDNA that encoded the variable heavy and light chains was amplified by polymerase chain reaction using degenerate primer sequences specific for each cDNA. The variable heavy chain cDNA was digested with restriction enzymes that were added during the PCR reaction and the products of this reaction were cloned into an IgG2 expression vector with compatible overhangs for cloning. This vector was generated by cloning the constant domain of human IgG2 into the multiple cloning site of pcDNA3.1+/Hygro (Invitrogen, Burlington, Ontario, Canada). The variable light chain cDNA was digested with restriction enzymes that were added during the PCR reaction and the products of this reaction were cloned into an IgKappa expression vector with compatible overhangs for cloning. This vector was generated by cloning the constant domain of human IgK into the multiple cloning site of pcDNA3.1+/Neo (Invitrogen). The heavy chain and the light chain expression vectors were then co-lipofected into a 60 mm dish of 70% confluent human embryonal kidney 293 cells and the transfected cells were allowed to secrete a recombinant antibody with the identical specificity as the original plasma cell for 24 hours. The supernatant (3 mL) was harvested from the HEK 293 cells and the secretion of an intact antibody was demonstrated with a sandwich ELISA to specifically detect human IgG.

Example 6

Structural Analysis of the Anti-Matriptase Antibodies

An alignment of the Anti-Matriptase antibodies is shown below in Table 5.

were washed five times with dH2O. A goat anti-human IgG Fc-specific HRP-conjugated antibody was added at a final concentration of 1 µg/mL for 1 hour at RT for the secretion and the two binding assays. The plates were washed five times with dH2O. The plates were developed with the addition of tetramethylbenzidine (TMB) for 30 minutes and the ELISA was stopped by the addition of 1 M phosphoric acid.

Each ELISA plate was analyzed to determine the optical density of each well at 450 nm. The data is shown as the last dilution of the lipofection supernatant that gave a signal above

TABLE 5

Heavy Chain

| Well | Single Cell | Seq ID NO: | V Heavy/D/J | FR1 | CDR1 | FR2 |
|---|---|---|---|---|---|---|
|  |  | 11 | Germline | EVQLLESGGGLVQPGGSLRLSCAAS | GFTFSSYAMS | WVRQAPGKGLEWVS |
| 342A7 | 95 | 4 | VH3-23/DE-6/JH4B | EVQLLESGGGLVQPGGSLRLSCAAS | GFTFSSYAMS | WVRQAPGKGLEWVS |
| 298F7 | 136 | 8 |  | EVQLLESGGGLVQPGGSLRLSCAAS | GVTFSSYAMS | WVRQAPGKGLEWVS |

| Well | Seq ID NO: | V Heavy/D/J | CDR2 | FR3 | CDR3 | FR4 |
|---|---|---|---|---|---|---|
|  | 11 | Germline | AISGSGGSTYYADSVKG | RFTISRDNSKNTLYLQ MNSLRAEDTAVYYCAK |  | WGQGTLVTVSS |
| 342A7 | 4 | VH3-23/DE-6/ JH4B | AISSSGVNTHYADSVKG | RFTISRDNSKNTLYLQ MNSLRAEDTAVYYCAT | IASIALRGYYFDY | WGQGTLVTVSS |
| 298F7 | 8 |  | AISSSGGNTHYADSVKG | RFTISRDNSKNTLYLQ MNSLRAEDTAVYYCAT | IASIATRGYFFNY | WGQGTLVTVSS |

Light Chain

| Well | Single Cell | Seq ID NO: | V Kappa/J | FR1 | CDR1 | FR2 |
|---|---|---|---|---|---|---|
|  |  | 12 | Germline | EIVLTQSPGTLSLSPGERATLSC | RASQSVSSSYLA | WYQQKPGQAPRLLIY |
| 342A7 | 96 | 6 | A27/JK1 | EIVLTQSPGTLSLSPGERATLSC | RASQTFGSSYLA | WYQQKPGQAPRLLIY |
| 298F7 | 136 | 10 |  | DIVLTQSPGTLSLSPGERATLSC | RASQIFSSNSLA | WYQQKPGQAPSLLIY |

| Well | Single Cell | Seq ID NO: | V Kappa/J | CDR2 | FR3 | CDR3 | FR4 |
|---|---|---|---|---|---|---|---|
|  |  | 12 | Germline | GASSRAT | GIPDRFSGSGSGTDFT LTISRLEPEDFAVYYC |  | FGQGTKVEIK |
| 342A7 | 96 | 6 | A27/JK1 | GASSRAT | VIPDRFSGSGSGTDFT LTISRLEPEDFAVYYC | QQYGSSPWT | FGQGTKVEIK |
| 298F7 | 136 | 10 |  | GASSRAT | GIPDRFSGSGSGTDFT LTISRLEPEDFAVYYC | QQYGSSPWT | FGQGTKVEIK |

Example 7

Secretion ELISA Analysis

The specificity of anti-Matriptase antibodies was assessed through binding of each recombinant antibody to the biotinylated catalytic domain of Matriptase using an ELISA (Table 6). The secretion ELISA tests were performed as follows.

Control plates were coated with 2 mg/mL Goat anti-human IgG H+L O/N as for binding plates. A biotinylated form of the catalytic domain of Matriptase (1 µg/mL) was coated onto Streptavidin 96-well plates (BD Biosciences, Bedford, Mass.) for 30 minutes. The plates were washed five times with dH2O. Recombinant antibodies were titrated 1:2 for 7 wells from the undiluted lipofection supernatant. The plates background. A signal of greater than 1:64 indicates that the sample had a signal above background at the largest dilution (64-fold) tested in the assay.

TABLE 6

Secretion and Binding Data of the Recombinant Antibodies

| Well ID | | Single Cell | | | Recombinant |
|---|---|---|---|---|---|
| Plate | Well | (sc) Numbers | Secretion | Binding | Ab Number |
| 298 | F7 | sc-135-154 | >1:64 | >1:64 | sc-136 |
| 351 | D2 | sc115-134 | >1:64 | >1:64 | sc116 |
| 342 | A7 | sc-95-114 | 1:64 | 1:8 | sc-95γ/96κ |
| 345 | G10 | sc77-94 | >1:64 | >1:64 | sc79 |

Example 8

Purification of Recombinant Antibodies

For larger scale production of the anti-Matriptase antibodies, heavy and light chain expression vectors (2.5 µg of each chain/dish) were lipofected into ten 100 mm dishes that were 70% confluent with HEK 293 cells. The transfected cells were incubated at 37° C. for 4 days, the supernatant (6 mL) was harvested and replaced with 6 mL of fresh media. At day 7, the supernatant was removed and pooled with the initial harvest (120 mL total from 10 plates). The antibodies were purified from the supernatant using Protein-A Sepharose (Amersham Biosciences, Piscataway, N.J.) affinity chromatography (1 mL). The antibodies were eluted from the Protein-A column with 500 mcL of 0.1 M Glycine pH 2.5. The eluate was dialyzed in PBS pH 7.4 and filter sterilized. The antibodies were analyzed by non-reducing SDS-PAGE to assess purity and yield. Protein concentration was determined by determining the optical density at 280 nm.

Example 9

Immunohistochemical Analysis

Immunohistochemical (IHC) analysis of Matriptase expression in tumor cells and specimens was performed using techniques known in the art. Fully human anti-Matriptase antibody sc95/96 IgG2 was used for the analysis.

Briefly, tumor specimens were deparaffinized using conventional techniques. Sections were incubated with 10% normal goat serum for 10 minutes. Normal goat serum solution was drained and wiped to remove excess solution. Sections were incubated with anti-Matriptase mAb at 10 µg/ml for two hours at 25° C., and washed thoroughly with PBS. After incubation with a secondary antibody conjugated to HRP, a solution of 3-amino-9-ethylcarbazole (AEC) was applied to the sections to visualize the immunoreactivity. For the isotype control, sections were incubated with an isotype matched negative control antibody (PK 16.3) at 10 µg/ml for two hours at 25° C.

Positive staining with the anti-Matriptase mAb was observed on T47D breast cancer cells, which are known to endogenously express Matriptase (Lin et al., 1997, Journal of Biological Chemistry, 272:9147-9152). Positive Matriptase staining was also observed on a human breast cancer specimen. No staining was observed with the isotype control antibody.

Example 10

Biacore Affinity Analysis of the Recombinant Anti-Matriptase Antibodies

The label-free surface plasmon resonance (SPR) method, also known as "Biacore", was utilized to measure the binding affinity of the Anti-Matripase antibodies Sc95/96 and Sc136 to the antigen. The recombinant antibodies Sc95/96 and Sc136 were immobilized onto a CM5 Biacore chip using standard amine coupling as shown below at densities of 250 RU.

The catalytic domain of Matriptase starting concentration of 1 mg/mL (37.8 µM) was diluted to 12.3 nM in Hanks buffered saline +0.1% BSA and run in a three fold concentration series in quadruplicate. Bound complexes were regenerated with a 15 s pulse of 1/200 phosphoric acid. The flow rate was 25 µl/min. The association contact time was 5 minutes. Results of the assay are shown below in Table 7.

Long dissociation phase data were collected for the 12.3 nM antigen concentration using a dissociation time of 1 hour in quadruplicate. The short term and long term binding data were fit together using a mass transport limited model to determine the binding rate constants reported below in Table 7.

TABLE 7

| mAb | $k_a$ (M$^{-1}$s$^{-1}$) | $k_d$ (s$^{-1}$) | $K_D$ (pM) |
| --- | --- | --- | --- |
| Sc95/96 | 5.87e5 ± 300 | 1.17e−5 ± 3e−8 | 19.9 ± 0.05 |
| Sc136 | 6.64e5 ± 400 | 2.74e−5 ± 6e−8 | 41.3 ± 0.1 |

Example 11

Method of Ki Determination

Ki is a measure of binding affinity of a molecule towards another molecule. To determine the Ki of the recombinant anti-Matriptase antibodies toward the Matriptase protein, the following method was used.

The anti-Matriptase antibodies were pre-incubated at various picomolar range concentrations with a fixed amount of Matriptase (1000 pM) diluted in 100 mM Tris Cl pH 8.5 for 1 hour at room temperature with shaking. QAR-MCA was added at various concentrations in the micromolar range. Binding was detected and measured using the kinetic read module of FL600 fluorimeter, with the detection at 360/460 nm. Initial velocity ($V_o$) measurements were collected at early time points (FU/time) at 37° C. for 45 minutes. The $V_o$ corresponded to the greatest slope in the plot of FU over time at initial time points. The $V_o$ was then tabulated at different antibody concentrations versus QAR-MCA concentration. At an antibody concentration=0 pM, Km and Vmax was obtained by using the Michaelis-Menten plot. Sigma Plot was then used to perform a non-linear least square regression to fit the "Tight Binding Inhibition Model", which obtains Ki and [E]o The Tight Binding Equation is shown below:

$$\frac{v}{v_o} = \frac{[E]_o - [1] - Ki_{app} + sqrt(([E]_o - [1] - Ki_{app})^2 + 4[E]_o Ki_{app})}{2[E]_o}$$

The calculated ki is shown below in Table 8:

TABLE 8

|  | Ki of sc95/96 (pM) | Ki of sc136 (pM) |
| --- | --- | --- |
| n = 1 | 13.4 | 12.0 |
| n = 2 | 16.0 | 10.0 |
| n = 3 | 18.2 | ND |
| n = 4 | 8.3 | ND |
| Average | 14.0 | 11.0 |
| St. Dev. | 4.3 | 1.4 |

The resulting Ki of the recombinant anti-Matriptase antibody sc95/96 ranged from about 8 pM to about 18 pM, with an average of about 14 pM. Similarly, the Ki of the recombinant anti-Matriptase antibody sc136 ranged from about 10 pM to about 12 pM, with an average of about 11 pM.

Example 12

Single-Chain Urokinase-Type Plasminogen Activator (Pro-Urokinase) (Sc-UPA) Inhibition Assay As mentioned earlier, Matriptase has been shown to cleave several enzymes, including the single chain Urokinase-Type Plasminogen Activator (sc-uPA) (Toshihiko et al., 2000, supra). This cleavage results in the conversion of sc-uPA, an inactive zymogen, into two-chain Urokinase plasminogen activator (tc-uPA), the active enzyme. The activity of tc-uPA can be determined by its ability to liberate AMC from its MCA-substrate known as Spectrozyme. To determine to what extent the anti-Matriptase antibodies were capable of inhibiting this cleavage activity by binding to Matriptase, the following assay was performed. 25 µl of Matriptase-1 was incubated with 15µl recombinant antibody in 100 mM Tris Cl pH 8.5 for 30 minutes at room temperature with shaking. Titrated concentrations of antibody (16000 pM, 8000 pM, and 4000 pM) were incubated with fixed amounts of Matriptase-1 at 1000 pM. 10 µl of 0.75 µM scuPA (Cortex Biochem, San Leandro, Calif.) was added to the reaction, and the mixture was incubated for 1 hr at 37° C. without shaking. 10 µl of 275 µM fluorogenic spectrozyme was then added and the reaction was measured immediately at 360/460 nm.

The results of the assay are shown below in Table 9. The background has been subtracted to yield a measurement of corrected fluorescence units (FU=Fluorescence units). The results show that antibodies sc136 and sc96/95 were able to inhibit Matriptase enzyme activity by approximately 90%.

TABLE 9

| | Corrected F.U. | | % |
|---|---|---|---|
| | n = 1 | n = 2 | inhibition |
| [sc136 IgG2] antibody conc (pM) | | | |
| 16000 | 2685 | 2542 | 89 |
| 8000 | 2435 | 2514 | 89 |
| 4000 | 2313 | 2350 | 90 |
| 0 | 23142 | 22528 | 0 |
| [sc96/95] antibody conc (pM) | | | |
| 16000 | 2704 | 2527 | 89 |
| 8000 | 2319 | 2423 | 90 |
| 4000 | 2462 | 2408 | 90 |
| 0 | 23215 | 23694 | 0 |
| [IgG2 isotype control] antibody conc (pM) | | | |
| 16000 | 30060 | 29383 | −24 |
| 8000 | 26599 | 26804 | −12 |
| 4000 | 27884 | 26184 | −13 |
| 0 | 23746 | 24045 | 0 |

Example 13

Antibody Binding to Native Matriptase (MTSP-1) Expressed on 22Rv1 Cells

To determine the extent of binding of the anti-Matriptase antibodies sc136IgG1 and sc95/96 IgG1 to the native Matriptase protein when expressed on the cell surface, the following assay was performed. Purified anti-Matriptase antibodies sc136IgG1 and sc95/96 IgG1, at a concentration of 1 µg/ml, were incubated with cells from the human prostate carcinoma cell line 22Rv1 that express native MtSP-1. The results, compared to that of an IgG1 irrelevant control antibody, were determined as follows.

The shift in fluorescence of the cells due to the binding of antibodies against Matriptase to the cell surface was determined by FACS. A greater shift indicates more antibody to the cells. The geomean was around 210 for sc95/96 and sc136 compared with around 5 for the irrelevant control antibodies, indicating binding to native Matriptase protein.

Example 14

Cross-reactivity to Rhesus Macague MTSP-1 on 4MBr5 Cells

To determine the extent of cross-reactivity of the anti-Matriptase antibodies scl36IgG1 and sc95/96 IgG1 with Matriptase orthologs, the binding of anti-Matriptase antibodies to monkey primary lung epithelial cells, 4MBr5, was determined using FACS. The binding of purified sc136IgG1 and sc95/96 IgG1 was measured and compared to that of an IgG1 irrelevant control antibody. All antibody concentrations were performed at 1 µg/ml. The results, compared to that of an IgGI irrelevant control antibody, were determined as follows.

The shift in fluorescence of the cells due to the binding of antibodies against Matriptase to the cell surface was determined by FACS. A greater shift indicates more antibody binding to the cells. The geomean was approximately 298 for sc95/96 and approximately 288 for sc136 compared with approximately 5 for the irrelevant control antibodies.

These results demonstrate that the anti-Matriptase antibodies recognize a protein expressed on the cell surface of 4MBr5 cells and indicate that the antibodies cross-react with a protein from rhesus macaques that is likely their ortholog of human Matriptase.

Example 15

Inhibition of Migration Assay

As mentioned earlier, Matriptase is thought to be involved in allowing the migration of cancer cells to new locations in the body. To examine whether the presence of anti-Matriptase antibodies can inhibit cellular migration, the following assay was performed.

The 8 µM Quantitative Cell Migration pre-coated plates (Chemicon, Temecula, Calif.) were prepared. Serum-free media was warmed to 37° C. and plates were then brought to room temperature. 300 µl of pre-warmed media was added to the upper chamber of each well. The plates were incubated at room temperature for two hours.

While the ECM was setting, cells of the human choriocarcinoma cell line JEG-3 (ATCC, Manassas, Va.) or the prostate carcinoma cell line 22Rv1 (ATCC, Manassas, Va.) were prepared as follows. The cells were removed from the flask using cell dissociation buffer (SIGMA, St. Louis, Mo.). The cells were then washed 3× with pre-warned serum free media, and the cells were counted using trypan blue stain. The cells were then re-suspended in serum free media at $2 \times 10^5$ cells/300 µL.

When the ECM was set and cells were prepared, 500 µl serum free media, or media with 10% FCS, was added to the lower chamber of each well. 10 µg/mL IgG2 isotype control or antibody sc95/96 was added to the appropriate wells. The 22Rv1 or JEG-3 cells were then added to the upper chamber (300 µl at $2 \times 10^5$ cells/300 µl). Then, 10 µg/mL of IgG2 isotype control or sc95/96 was added to appropriate wells. The wells were incubated at 37° C./5% $CO_2$ for 24 hrs.

After 24 hours, the gradient was re-established for the appropriate wells. The media was carefully removed from the bottom chamber and replaced with 500 µl of either pre-warmed serum free media or media +10% FBS. The media was carefully removed from the upper chamber and replaced with 300 µl pre-warmed serum free media. The wells were incubated at 37° C. in 5% $CO_2$ for 24 hours.

Figure 1B:
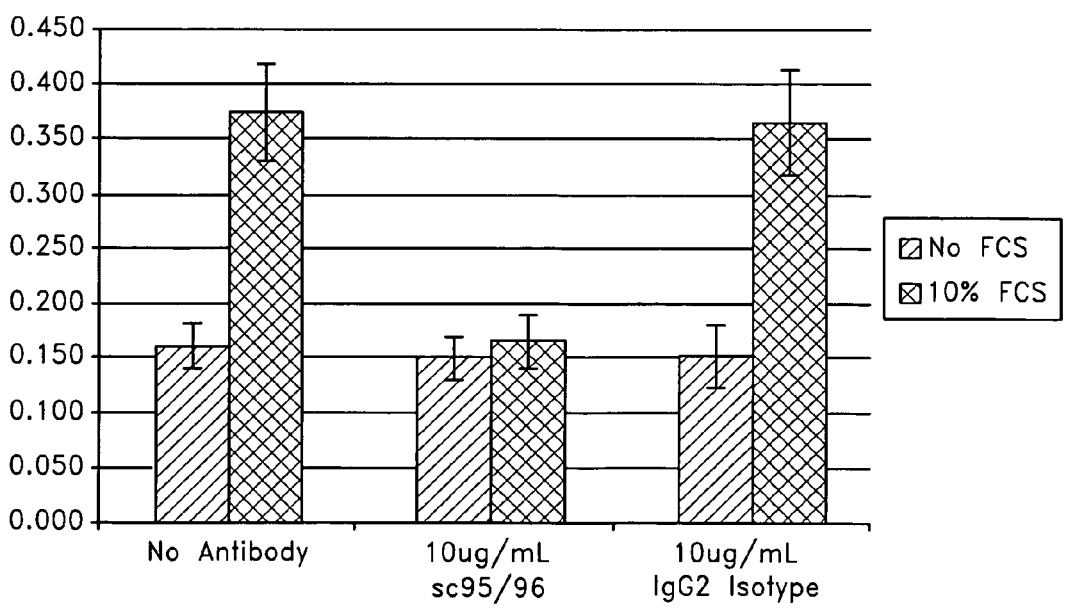

Samples were then prepared for visualization and quantitation analysis. The media was removed from the top chamber of each well using a pipette. The Matrigel was then removed from the top of the membrane using a pre-wetted cotton swab using a twisting motion. The ECM and any remaining cells that did not migrate to the membrane were removed. As crystal violet stains cells, one can solubilize the stained cells and quantitated the relative cell number by taking an absorbance reading at 600 nm. For crystal violet extraction, 200 µl 10% acetic acid was added to each insert, the contents were removed, and placed in a 96-well flat bottom plate. Inhibition of migration was measured using both 22Rv1 cells (FIG. 1A) and JEG-3 cells (FIG. 1B). The data shows that anti-MTSP1 antibodies can prevent the migration of JEG-3 and 22Rv1 cells in response to an FCS gradient.

Example 16

Detection of Matriptase on B Cells

In order to assess the expression of Matriptase and its cognate inhibitor HAI-1 in B cell cancer lines, sc95/96 and goat anti HAI-1 polyclonal antibodies were used in the following assay.

Three Burkitt's lymphoma cell lines (Daudi, Raji, Ramos) were grown in standard conditions. Non-adherent cells were removed from tissue culture dishes and seeded into vee bottom plates at a concentration of 300,000 cells per well. The cells were then incubated on ice with sc95/96 or with a goat anti HAI-1 polyclonal antibody for 1 hr. After the incubation the cells were washed twice with PBS/2% FCS buffer and then incubated with secondary Cy5 labeled anti-species antibody for 15 min on ice. After the incubation the cells were washed twice with PBS/2% FCS buffer and binding was quantified using FACS.

Figure 2:
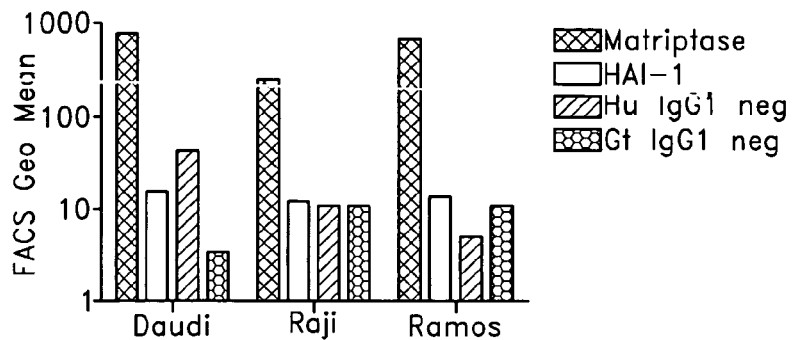
FIG. 2 is a bar graph showing the expression of Matriptase and HAI-1 in B cell cancer lines.

Expression of Matriptase was also confirmed in a primary lymphoma sample via IHC. These data show that the tested B cell cancer cell lines express high levels of Matriptase and very little (if any) HAI-1 (FIG. 2). This is in contrast to epithelial cell lines which express moderate to high levels of HAI-1.

Example 17

Detection of Matriptase on Normal Peripheral Blood Cells

To assess the expression of Matriptase and HA-1 on normal peripheral blood cells, the following assay was performed.

Normal peripheral blood monocytes were isolated using Ficoll density centrifugation, and aliquoted into vee bottom plates. Cells were centrifuged at 400×g for 3 minutes and the supernatant was carefully removed using a multichannel pipette. Cells were resuspended with 5 µg/mL Biotinylated Human anti-Matriptase mab (sc95/96), Goat anti-HAI-1 pab or isotype matched controls, and then diluted in FACS buffer (PBS/2% FCS). Cells were then incubated on ice for 1hr, and following the incubation cells were washed twice with FACS buffer. Cells were then resuspended with 100 µL anti CD19 (1:5 Dilution), 7AAD (10 ug/mL), SA-FITC (Sug/mL), and anti Gt Cy5 (5 ug/mL), and then incubated on ice for 15 minutes.

Following the 15 minute incubation, cells were washed 2× with FACS buffer, and then resuspended in 200 µL cold FACS buffer and transferred to pre-labeled FACS tubes containing 100 µL FACS buffer.

Figure 3:
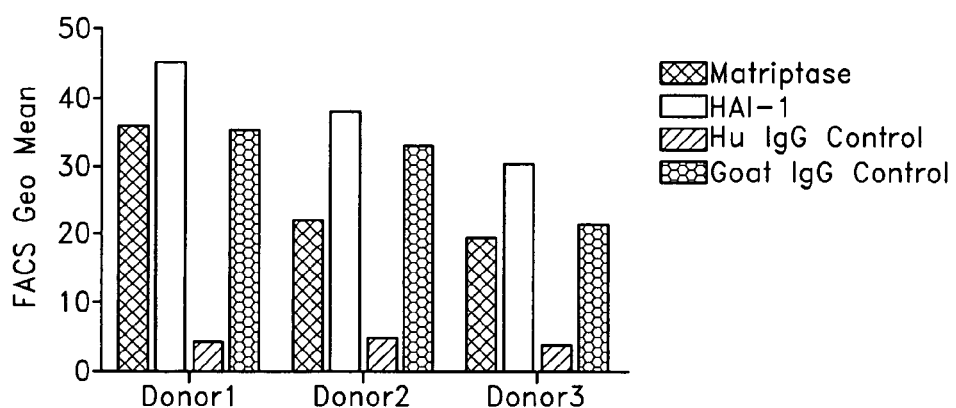
FIG. 3 shows bar graphs representing the expression of Matriptase and HAI-1 in peripheral blood CD19+ B cells (top) and peripheral blood monocytes (bottom).
Figure 3:
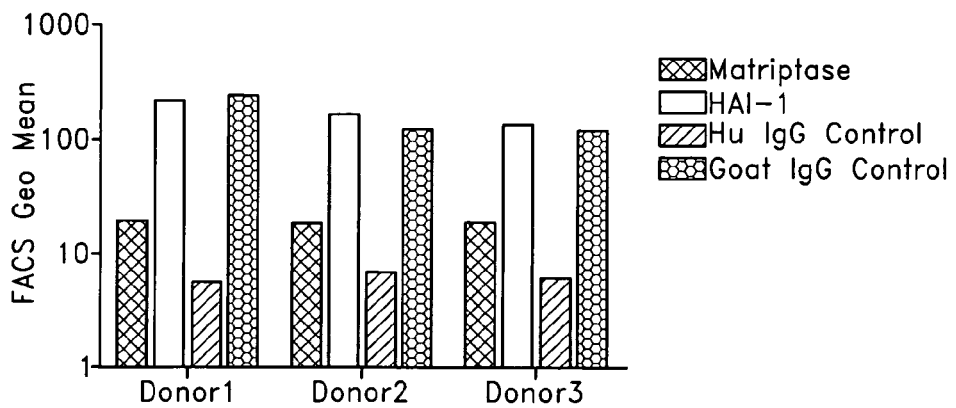

Samples were analyzed using flow cytometry. B cells were identified using the CD19 counterstain (FIG. 3, top). Monocytes were defined as the population of cells with high forward and side scatter (FIG. 3, bottom).

Expression of Matriptase was also confirmed in a primary lymph node sample via IHC. It is clear from these data that there is low level expression of Matriptase in CD19 positive B cells and monocytes. There is very little (if any) expression of HAI-1 in the CD19 population, and undetectable expression in the monocyte population.

Example 18

Matriptase On-cell Activity Assay

MT-SP1 is often expressed with its inhibitor HAI-1, which tightly regulates the activity of MT-SP1. Additionally, the protease requires cleavage to become fully active, suggesting that the expression of MT-SP1 alone doesn't confer enzymatic activity. The use of an on-cell activity assay would allow for the identification of appropriate cell lines to use to help determine the function of MT-SP1 in vivo. To determine if MT-SP1 activity could be detected on the cell surface of cancer cell lines, the following assay was performed.

For adherent cell lines, supernatant was removed from cells and cells were then washed with PBS (pH7.4). PBS was subsequently removed and cell dissociation buffer was added to cells and incubated for 5 minutes at 37 degrees. Cells were then removed from flask into a 50 mL Falcon tube.

Suspension cells were also transferred from their culture flask into a 50 mL Falcon tube. Both suspension and adherent cells were spun at 1500 rpm for 3 minutes, after which the cells were washed three times using media and then resuspended with media. Cells were then counted using a haemocytometer and Trypan Blue. A half-plate titration of the cells was performed. In other words, cells were seeded at $1×10^6$ cells in the $1^{st}$ and $7^{th}$ well of a 96-well plate and titrated 1:2 in a volume of 150 µL, leaving the $6^{th}$ and $12^{th}$ well blank. To each well, 25 L of antibody (7 µg/mL) was added, so that the final antibody concentration was 1 µg/mL. The cell/antibody mixture was incubated for 1 hour at 37 degrees.

Figure 4:
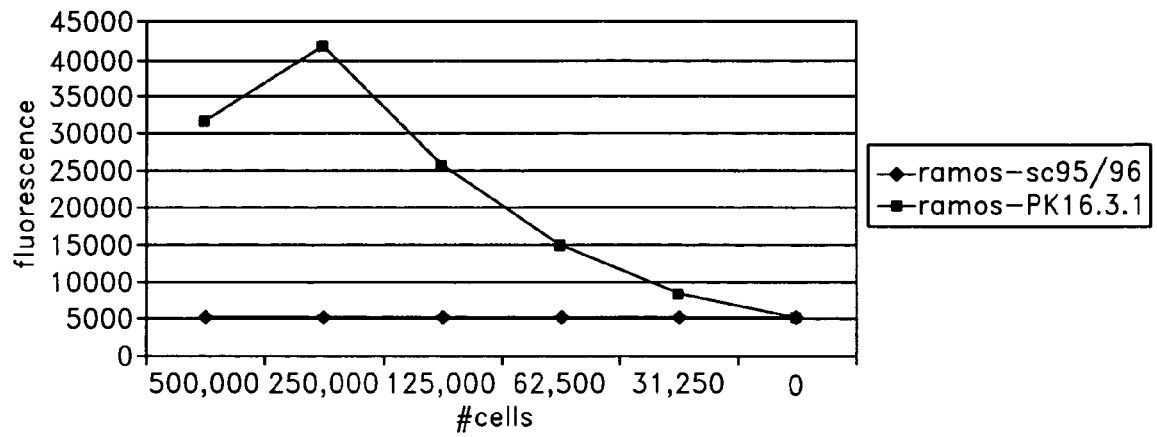
FIG. 4 is a line graph presenting the results of an on-cell protease activity assay using Ramos cells in the presence of either sc95/96 or a control antibody.

After 1 hour, 25 µL of tripeptide substrate (400 µM) was added to each well so that the final substrate concentration was 50 µM. The plate was then read on a TECAN reader at 0, 1, 2, 3, and 4 hour and overnight time points. The results are presented in FIG. 4.

The on-cell activity assay clearly demonstrated the presence of a protease activity on the surface of Ramos cells. This activity was completely inhibited by sc95/96, suggesting that this activity is due to MT-SP1.

Example 19

Effect of sc95/96 in the Ramos Hind-Limb Paralysis Model

The ability of sc95/96 to modulate the invasive and/or metastatic properties of Ramos cells was evaluated in a rodent hind-limb paralysis model. Without therapeutic intervention, SCID mice inoculated systemically with Ramos B lymphoma cells develop hind limb paralysis at ~25 days post injection, presumably related to the accumulation of tumor cells in the spinal cord and/or brain tissues (dijoseph et al., 2004, Clinical Cancer Research 10: 8620-8629).

In this experiment, 7-8 week old C.B-17 SCID male mice were inoculated with $1 \times 10^6$ Ramos cells via tail vein injection. One day later, 4 groups of 10 mice, randomized by order of injection, received either a 75 mg/kg loading dose of sc95/96 (IgG1), a 75 mg/kg loading dose of an isotype-matched control antibody KLH120.6.1, an equivalent volume of saline control (PBS) or a 5 mg/kg dose of Rituximab (Table 10) via i.p. injection. Groups 1-3 thereafter received weekly 25 mg/kg injections of antibody or an equivalent volume of PBS. Animals were given food and water ad libidum and monitored daily for signs of paralysis. Individual mice were euthanized when unable to move due to hind limb paralysis.

TABLE 10

| Group number | Group size | Treatment | Dose | Schedule | Loading | Route |
|---|---|---|---|---|---|---|
| 1 | 10 | PBS | N/A | q7d | 3x vol | ip |
| 2 | 10 | KLH 120.6.1 | 25 mg/kg | q7d | 3x | ip |
| 3 | 10 | sc95/96 | 25 mg/kg | q7d | 3x | ip |
| 4 | 10 | Rituximab | 5 mg/kg | d1 | none | ip |

Figure 5:
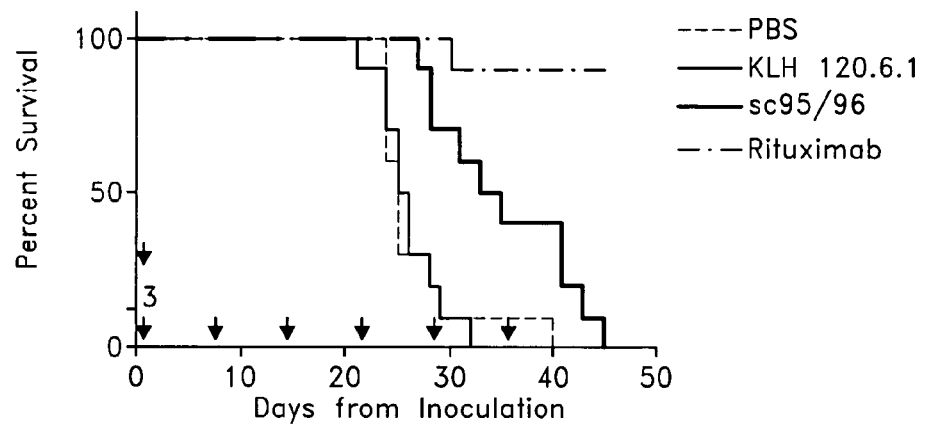
FIG. 5 is a line graph showing survival for Ramos tumor-bearing SCID mice treated with either PBS, KLH 120.6.1, sc95/96, or Rituximab.

Survival data for the four groups of mice is shown in FIG. 5 (lower arrows indicate treatment days for groups 1-3, upper arrow indicates treatment day for group 4). Median.survival times were 25 days for the PBS group, 26 days for the KLH 120.6.1 group, 35 days for the sc95/96 group and greater than 45 days for the Rituximab group.

In this experiment, a 25 mg/kg weekly dose of sc95/96 was found to significantly ($p<0.01$) extend the median survival of Ramos tumor-bearing SCID mice. These data suggest a role for MT-SPI catalytic activity in the invasion or metastasis of Ramos B cell lymphoma and furthermore demonstrate the ability of sc95/96 to modulate this pathologic process.

Example 20

Effect of sc95/96 in CDC Assay

As sc95/96 showed efficacy in the in vivo studies, further experiments were performed to explore different potential mechanisms of action of the antibody. The antibody was already well-established for its ability to neutralize MTSPI activity, but its potential role in complement-mediated cytolysis was unknown.

Figure 6A:
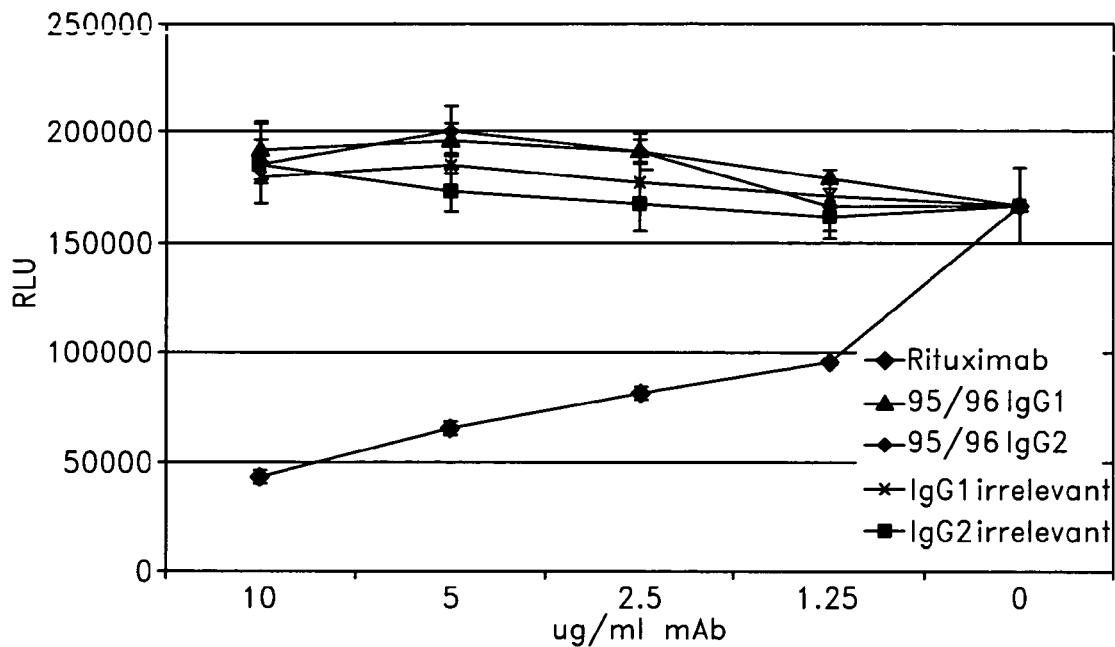
FIG. 6A is a line graph showing the results of an assay that measures complement-dependent cytolysis (CDC) of Ramos cells in the presence of sc95/96 IgG1, sc95/96 IgG2, or control antibodies, where increased luminescence (RLU) indicates cell survival.
Figure 6B:
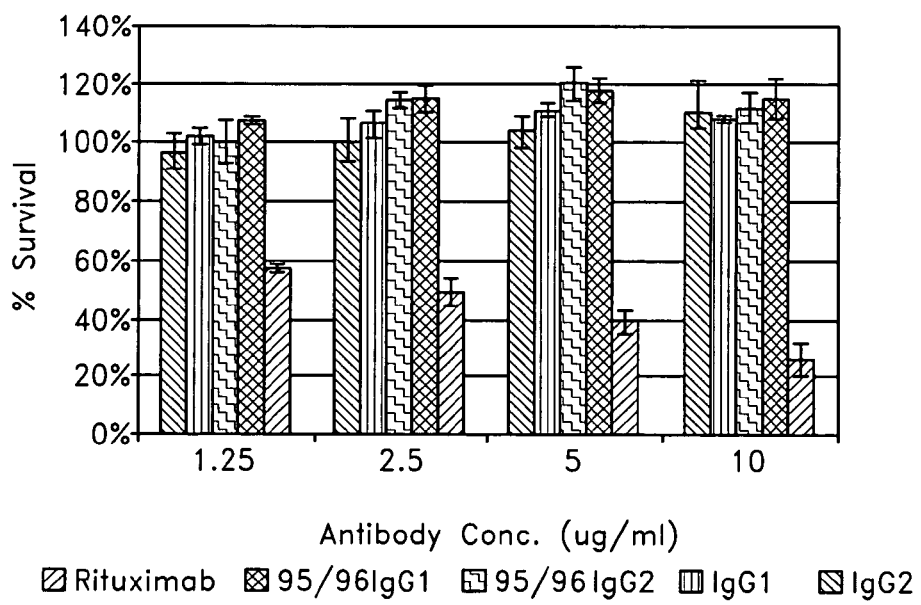
FIG. 6B is a bar graph depicting the results of FIG. 6A as percent survival.

In this experiment, 100,000 Ramos cells in 25 μL of media were added to the bottom of a 96-well plate. To this, 25 μL of a four times stock of sc95/96 was added such that the final concentrations of 10, 5, 2.5 and 1.25 μg/mL would be achieved. Each sample point was run in quadruplicate. After 10 minutes at room temperature, 50 μL of 50% human sera (25% final concentration) was added to the cells and incubated at 37 degrees Celsius for 1 hour. CellTiterGlo reagent (100 μL) was added to each well and allowed to incubate on the cells for 10 minutes. The cell survival was determined by luminescence reading on a Tecan reader, and the results are shown in FIGS. 6A and 6B.

sc95/96 did not induce CDC on Ramos cells as either an IgG1 or IgG2 antibody. This result indicates that CDC-activity is unlikely to be one of the mechanisms of action to explain the observed efficacy in the Ramos study. The positive control antibody Rituximab did demonstrate CDC activity on Ramos cells as expected.

Example 21

Function of sc95/96 in the Whole Blood Assay

As sc95/96 showed efficacy in the in vivo studies, additional experiments were performed to explore different potential mechanisms of action of the antibody. The antibody neutralizes MTSP1 activity and fails to work in CDC assays, but its potential role in whole blood assay (CDC and antibody-dependent cellular cytotoxicity) was unknown.

Target cells (Ramos, Raji) were harvested and resuspended in media at $1 \times 10^6$ cells/ml, for a final density of $1 \times 10^6$ cells/plate. Calcein AM (Sigma #C1359, St. Louis, Mo.) was then added to a final concentration of 15 μM (11.25 μL in 3 ml cells), and cells were incubated for 60 minutes at 37 degrees. While cells were incubating, antibodies were prepared for testing in a 96-well U-bottom plate (Costar #3799, Acton, Mass.).

After incubation, cells were pelleted by centrifugation at 1200 RPM for 10 minutes, the supernatant was discarded and the pellet was resuspended in media. This centrifugation step was repeated, and cells were resuspended to a final concentration of 10000 cells/100 μL. Target cells were plated in 96-well U-bottom plates at 100 L/well (Costar #3799, Acton, Mass.). Target cells were incubated with antibody for 30 minutes at 37 degrees. Whole blood (~18 ml) was collected in heparinized tubes from donors, and then 50 μL of whole blood was added to each well and then incubated for 4 hr at 37 degrees. After incubation, plates were centrifuged at 1200 RPM for 5 minutes, and 75 μL of supernatant was transferred to flat, black, clear-bottom plates (Costar #3603, Acton, Mass.). These plates were then read on a Victor plate reader using a 490 nm excitation and 530 nm emission wavelength.

Figure 7:
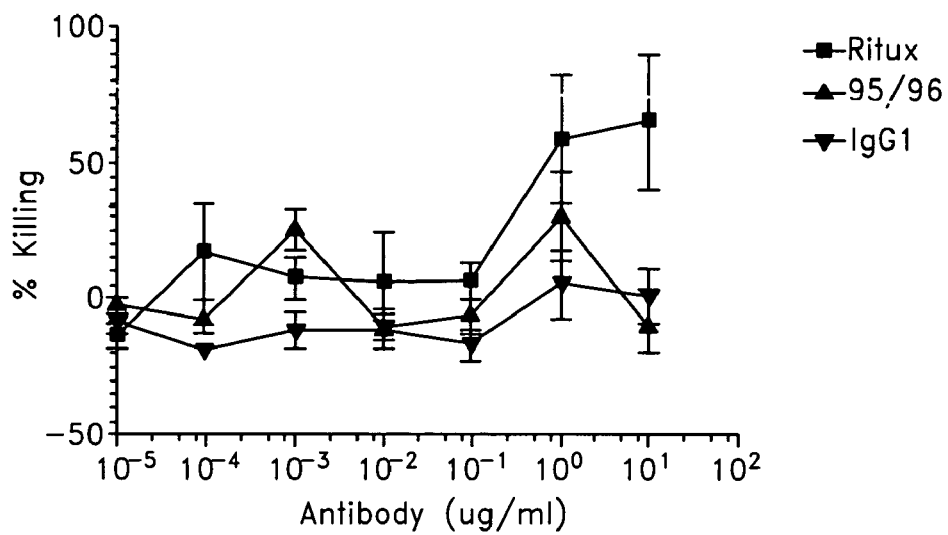
FIG. 7 is a line graph showing the results of a whole blood killing assay with Ramos as target cells.

These results, shown in FIG. 7, indicate that sc95/96 was unable to mediate cell killing in the whole blood assay. This finding supports the previous assay that indicated that the antibody was unable to mediate CDC and suggests that the antibody is also unable to mediate ADCC.

Example 22

Internalization of MT-SP1

To determine if sc95/96 can induce internalization of MT-SP1 on Ramos cells. As sc95/96 showed efficacy in the in vivo studies, experiments were performed to explore different potential mechanisms of action of the antibody. The antibody neutralizes MTSP1 activity and fails to work in CDC or whole blood assays, but its potential role in the internalization of cell surface MT-SP1 was unknown.

The following internalization assay was performed. 2 μg/ml of sc95/96 was pre-incubated with 2 μg/ml Gt Fab anti-human H@L-S-S-Alexa 647 in FACs buffer (2% FCS in PBS). Ramos cells were aliquoted at 200,000 cells per reaction, and were then washed once with 200 μL of FACs buffer. 100 μL of the pre-incubated sc95/96 mixture with Gt anti-human H@L-S-S-Alexa 647 were added to each reaction. Two tubes of each sample were incubated for 1hr at 4° C. and two tubes at 37° C., after which cells were washed once with 200 μL FACS buffer. Then, 100 μL of 200 mM Tris(2-carboxyethyl)phosphine hydrochloride (TCEP) were added to one sample at 4° C. and one sample at 37° C. and the samples were incubated for 1hr on ice. Finally, the cells were washed once with FACs buffer and read by FACS.

The percent internalization was determined from the geo-means above by the following equation:

% Internalization=((37° C.+TCEP)−(4° C.+TCEP))/
((4° C.−TCEP)−(4° C.+TCEP))×100

Figure 8:
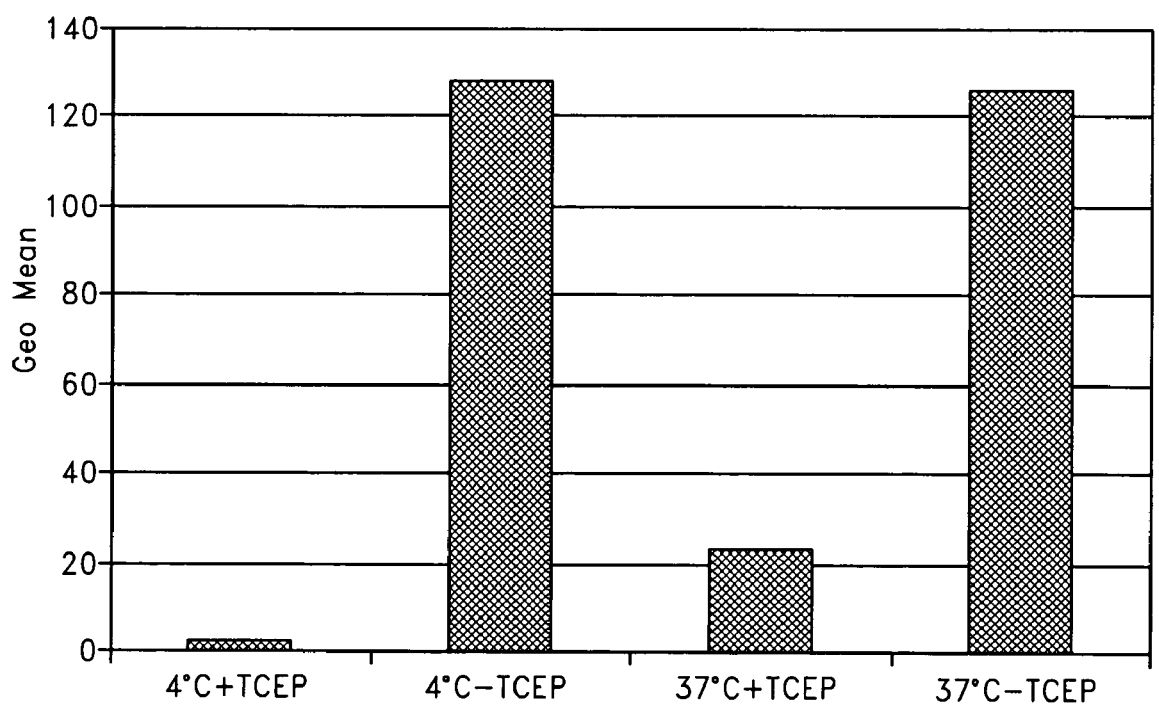
FIG. 8 is a bar graph showing the results of an assay measuring internalization of sc95/96 in Ramos cells.

The results (FIG. 8) indicated that 18% of the cell surface antibody was internalized through its interaction with MT-SP1 in one hour.

Thus, while the antibody can be internalized through its interaction with MT-SP1, only 18% of the cell surface protein has been removed from the cell surface. This is a possible mechanism of action of the antibody as the removal of MT-SPI from the cell surface would be expected to limit its interaction with its natural extracellular substrates.

Example 23

In Vitro Proliferation Assay

This antibody was shown to be unable to inhibit the proliferation of tumor cells in vitro. Because we had in vivo efficacy with the Ramos cells, it was important to determine if the antibody was able to show any in vitro efficacy on these particular cells.

For the proliferation assay, 100 μL per well of cells were seeded at 7×105 cells/ml and 2×105 cells/ml in media containing either 0%, 0.1% or 1% FBS. To each appropriate well, 100 μL of antibody, small molecule inhibitor or control at 2× final concentration, prepared in 0%, 0.1% or 1% FBS, was added. Cells were incubated at 37° C./5% $CO_2$ for 48 hr and viability was then determined using Alamar Blue.

Figure 9A:
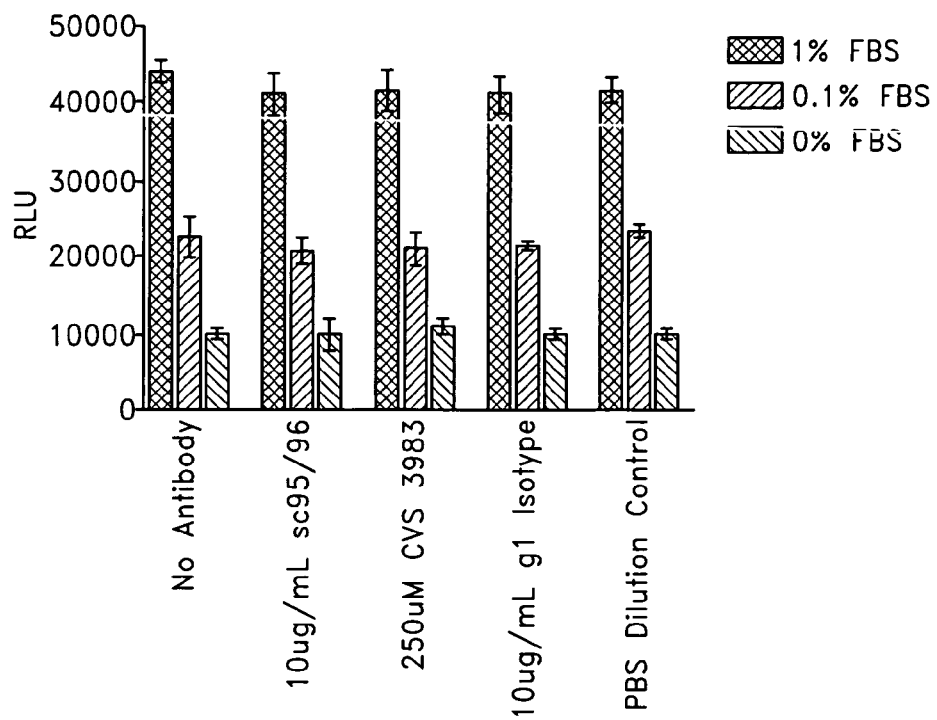
FIGS. 9A and 9B are bar graphs showing in vitro proliferation of Ramos cells at 200,000 (FIG. 9A) or 700,000 (FIG. 9B) cells/ml.
Figure 9B:
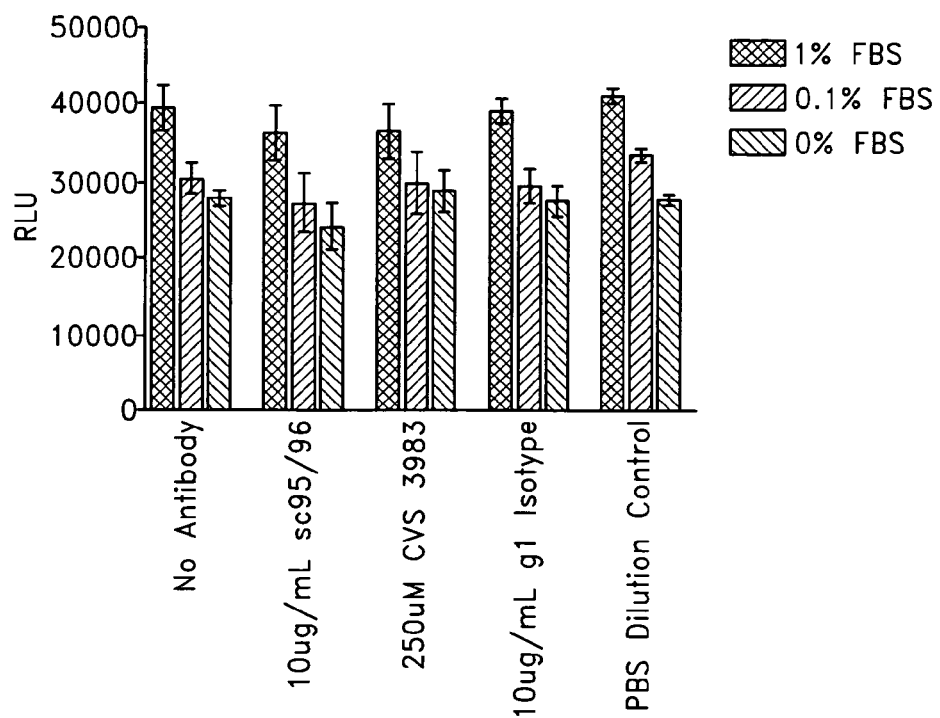

The results are shown in FIGS. 9A and 9B. The proliferation of Ramos cells was not affected by treatment with either the CVS-3983 compound or sc95/96. These data suggest that MT-SP1 is not involved in the in vitro proliferation of cells, although this data may not have much significance for in vivo proliferation of tumor cells.

Example 24

Invasion Assay

As mentioned earlier, some data suggest a role for MT-SP1 catalytic activity in the invasion or metastasis of Ramos B cell lymphoma and also demonstrate the ability of sc95/96 to modulate this pathologic process. This experiment was run to determine if MT-SP1 was involved in the in vitro invasion of cells into matrigel. If successful, this assay could also be used to identify cell lines for testing the in vivo utility of the antibody against MT-SP1.

In this experiment, $1.5 \times 10^5$ Ramos cells were added to the upper chamber of an 8 μm invasion well in serum-free media. Cells were then incubated for 48 hr at 37° C./5% CO2 in the presence or absence of 10% FBS in the lower chamber of the 8 μm invasion well (500 μL). Antibody (sc95/96 or g1 Isotype) was added to upper and lower chamber of appropriate wells at 10 μg/mL. CVS 3983 or PBS added to upper and lower chamber of appropriate wells (250 μM).

Following a 48 hr incubation, top chambers were removed and the media in the lower chamber was collected and spun down to reduce the sample volume. Samples were then counted on HIGH for 1min. All samples were tested on the same plate over 2 plates to obtain replicates of 4.

Figure 10:
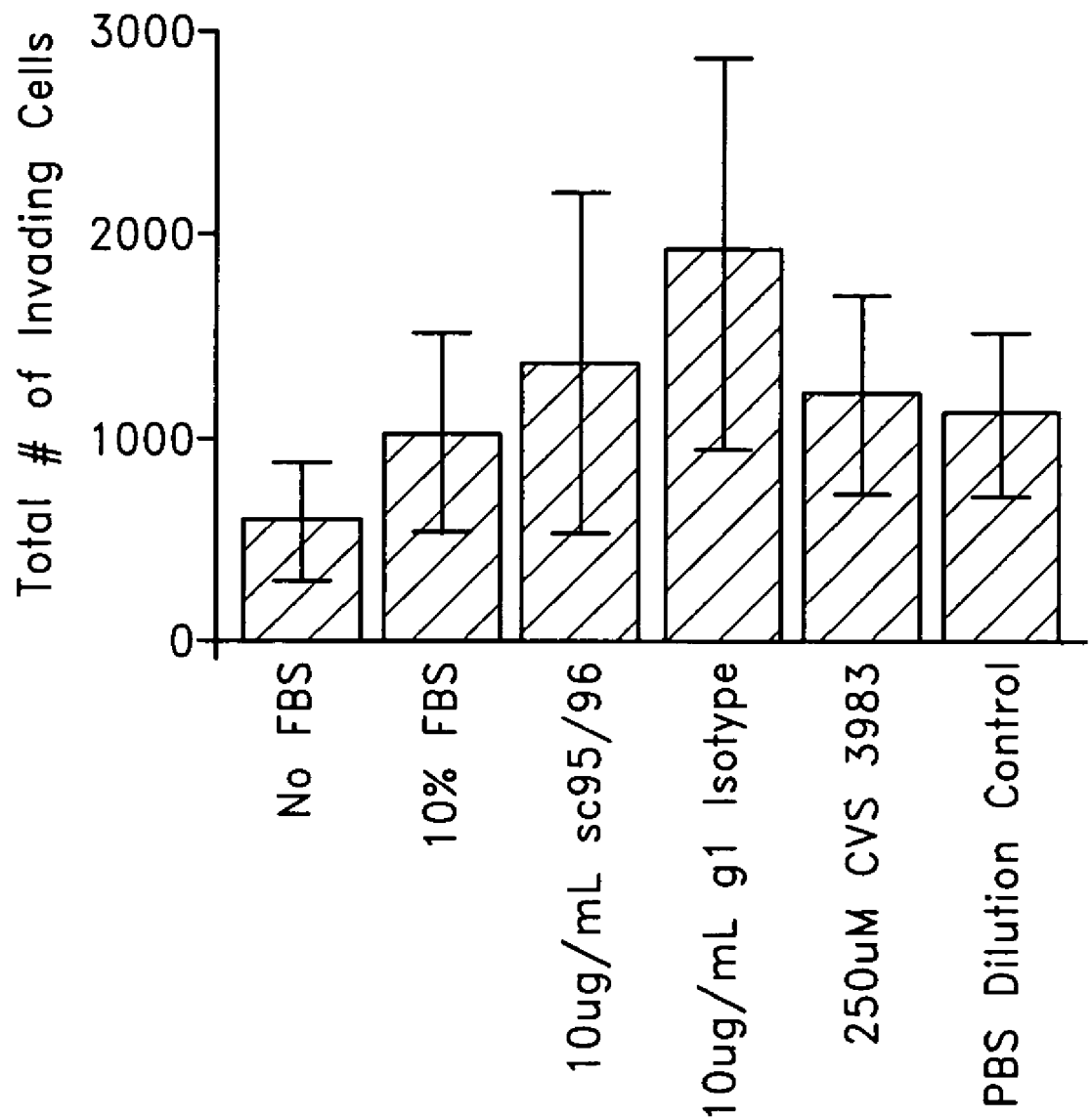
FIG. 10 is a bar graph that shows in vitro invasion of Ramos cells.

The results are presented in FIG. 10. The invasion of Ramos cells was not affected by treatment with either the CVS-3983 compound or sc95/96. These data suggest that MT-SP1 is not involved in the in vitro invasion of cells, although this data may not have much significance for in vivo invasion and metastasis.

Example 25

Competition Binding Assay

This experiment was set-up to determine whether or not HAI-1 (the natural inhibitor of MT-SP1) would compete for binding to MT-SP1 with 95/96. If the two proteins did compete with each other, it would suggest that 95/96 only binds to MT-SP1 that is not bound within the catalytic domain by HAI-1 (the interaction sites within other domains (ex. LDLR) need not be affected by the binding of 95/96).

125 ng/ml of Biotinylated-MTSP1 was incubated with sc95/96 or HAI-1 on a non-binding plate for 1 hour. HAI-1 was titrated from 2 μg/ml and sc95/96 was titrated from 10 μg/ml. After 1 hour, samples were transferred to a sc95/96 coated plate and incubated for 1 hour. Bound MTSP was then detected with SA-pod.

Figure 11:
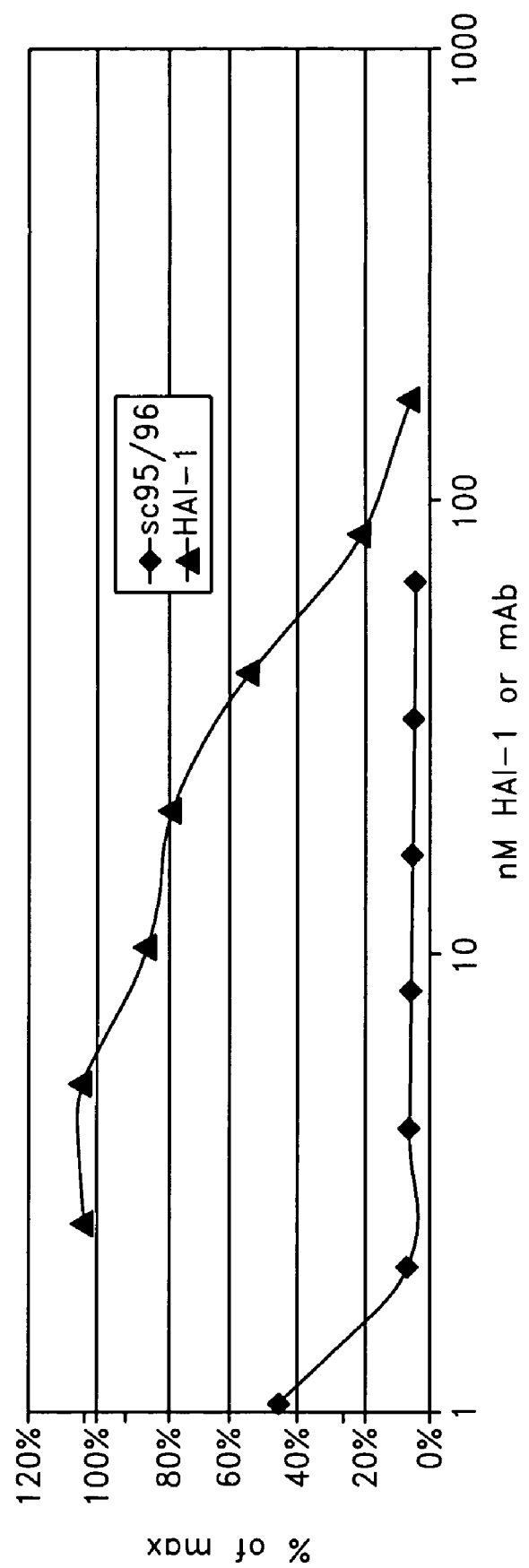
FIG. 11 is a line graph that shows the results of a competition binding assay for MT-SP1 binding to sc95/96.

The 95/96 antibody competed very effectively with itself for binding to biotinylated MT-SP1 demonstrating that the assay is working as expected (FIG. 11). Importantly, when MT-SP1 was incubated with HAI-1 prior to transfer onto a plate coated with 95/96 it prevented the binding of MT-SP1 to the plate. These data demonstrate that 95/96 and HAI-1 compete for over-lapping epitopes on MT-SP1.

Example 26

Surface Expression of Matriptase in Tumor Cell Lines

In order to compare surface expression of Matriptase and its cognate inhibitor HAI-1 in cell lines established from tumors of epithelial origin as well as hematological malignancies, a series of flow cytometry experiments were performed.

Epithelial tumor cell lines were chosen based on their previously described Matriptase expression. These lines included prostate cancer cell lines LNCaP and CWR22RVI and choriocarcinoma cell line JEG-3. Prostate cancer cell line DU-145, lacking expression of Matriptase, was used as a negative control.

Nine Burkitt's lymphoma cell lines, as well as other B cell lymphoma cell lines, T cell lymphoma lines, monocytic leukemia and other leukemia lines were selected (see below).

The cell lines were acquired from American Type Culture Collection (ATCC, Manassas, Va.) or European Collection of Cell Cultures (ECACC) and grown in standard conditions. Some lymphoblastoid cell lines (LCL) were generated by Dendreon from healthy donors. Cells were harvested for flow cytometry and washed with cold PBS containing 2% FBS. Prior to that, adherent cells (LNCaP, DU-145, CWR22RV1 and JEG-3) were washed with PBS and released from the growth surface with CellStripper (Mediatech, Hemdon, Va.) 24 hrs following their trypsinization and growth in non-tissue culture treated plastic dishes. For the staining, 5 μg/ml of matriptase-specific (sc95/96) or control (ABGX120) monoclonal antibodies were used. Staining was performed in PBS 2% FBS on ice for 60 min., followed by two washes and by 5 μg/ml of secondary reagent for 30 min. on ice. Fluorescently labeled polyclonal antibodies specific for human IgG (Molecular Probes Eugene, Oreg.) were used as a secondary reagent. After two washes, the cells were supplemented with 250 ng/ml of 7-Aminoactinomycin D (viability exclusion dye, Molecular Probes, Eugene, Oreg.) and evaluated in fluorescence activated cell sorter (FACSCalibur, Becton Dickinson, Franklin Lakes, N.J.) using CellQuest/CellQuest Pro software packages. In some experiments, antibodies ABGX120 and sc95/96 labeled with EZ-Link Sulfo-NHS-LC-Biotin (Pierce, Rockford, Ill.) were used, followed by fluorescently labeled Streptavidin (Molecular Probes, Eugene, Oreg.) used as a secondary reagent. HAI-1 was detected with a mouse monoclonal antibody specific for HAI-1 ectodomain (RnD Systems, Minneapolis, Minn.), followed by appropriate fluorescinated anti-mouse IgG reagent.

In the FACS staining experiments, strong surface staining of 9 out of 9 Burkitt's cell lines with Matriptase-specific antibody was observed (Table 11). None of the cell lines could be stained with HAI-1-specific antibody, in contrast to a prostate cancer cell line LNCaP, which showed the staining of both Matriptase and HAI-1. The expression of Matriptase in Burkitt's lymphoma line seemed substantially higher than epithelial cancer-derived cell lines tested.

TABLE 11

Expression of Matriptase and HAI-1 in Burkitt's lymphoma cell lines

| Cell line | Matriptase expression | HAI-1 expression |
|---|---|---|
| CA46 | + | − |
| Daudi | + | − |
| EB3 | + | − |
| GA10 | + | − |
| Jiyoyie | + | − |
| Namalwa | + | − |
| Raji | + | − |
| Ramos | + | − |
| ST486 | + | − |

This phenomenon was partially shared by some but not all other human lymphoma cell lines (Table 12). Particularly, some cell lines of B cell and monocytic origin expressed Matriptase. Of additional interest, the majority of human LCL cell lines were predominantly void of Matriptase expression, while retaining expression of HAI-1 (Table 13). This expression of HAI-1 was variable, and in some LCL lines quite substantial.

TABLE 12

Expression of Matriptase and HAI-1 in human lymphoma (non-Burkitt's) cell lines

| Cell line | Origin | Matriptase expression | HAI-1 expression |
|---|---|---|---|
| JM-1 | Pre-B cell | + | + |
| NALM-18 | Lymphoblastic | + | − |
| NALM-6 | Pre-B ALL | − | − |
| CCRF-SB | lymphoblastic | − | + |
| THP-1 | Acute monocytic | + | ND |
| MT2 | T cell leukemia, HTLV | − | ND |
| HUT-102 | T cell leukemia, HTLV | − | ND |
| JACT | T cell leukemia | − | + |
| CEM-NKR | T lymphoblastoid | − | − |
| K562 | Chronic myelogenous | − | − |
| KG1 | Acute myelogenous | − | ND |
| KM3 | Hematopoietic (myeloid) | − | +/− |
| SUP-B15 | Acute lymphoblastic | − | ND |
| HS445 | Hodgkin's | − | ND |
| Toledo | non-Hodgkin's | + | + |

TABLE 13

Expression of Matriptase and HAI-1 in human LCL cell lines

| | Matriptase | HAI-1 |
|---|---|---|
| AMAI | − | + |
| AMAUA | − | + |
| ARENT | − | − |
| BER | − | +/− |
| BM14 | − | + |
| BM15 | − | + |
| BM16 | − | + |
| BM21 | − | + |
| BM9 | − | + |
| BOB | + | + |
| EK | − | + |
| K5116 | − | + |
| LCL-LAJ | + | + |
| LKT3 | − | + |
| MSAB | − | +/− |
| OMW | − | − |
| PFAP | − | +/− |
| PMG075 | + | + |
| RMA | − | + |
| RSH | − | + |
| SKF | − | + |
| SPC | − | + |
| T7526 | − | + |
| TERND | − | + |
| TISI | − | + |
| VAVY | − | + |

Example 27

Effect of sc95/96 in ADCC Assay

As sc95/96 showed efficacy in the in vivo studies, it was important to explore different potential mechanisms of action of the antibody. The antibody neutralized MTSP1 activity but failed to work in CDC assays including a whole blood assay. Its role in antibody dependent cellular cytotoxicity (ADCC) remained unclear. In order to clarify the role of MTSP1 in ADCC, the following experiment was performed.

Raji cells were used as target cells for the ADCC assay. To prepare the target cells, Raji cells were harvested and resuspended in media at $1.0 \times 10^6$ cells/ml. Calcein (Sigma C1359) was then added to a final concentration of 10 µM, and the cells were incubated for 45-60 minutes at 37° C., after which the Raji cells were pelleted by centrifugation at 1200 rpm for 10 minutes. The supernatant was discarded and the cells were resuspended in growth media. The centrifugation step was repeated, the cells were resuspended at a concentration of $1.0 \times 10^4$ cells in 75µL media and were then plated at $1.0 \times 10^4$ cells per well in a round bottom plate. Then, mAb sc95/96, Rituximab, or control IgG1 antibody which had been serially diluted 1:10 was added to the appropriate well containing Raji cells for a final antibody concentration of 0.0001 to 1 µg/ml. The cells and antibody were incubated for 30 minutes at room temperature.

The effector cells for the ADCC assay were prepared as follows. Approximately 20 ml of whole blood was collected in heparin or EDTA-treated tubes, to which RosetteSep NK Cell Enrichment Cocktail (Stem Cell Technologies, catalog #15065) was added at a ratio of 50 µL per 1 ml whole blood. The mixture was incubated for 20 minutes at room temperature, after which the blood was diluted with an equal volume of PBS containing 2% FBS. 30 ml of the blood mixture was layered on to 15 ml of Ficoll-Paque PLUS (Amersham, catalog #17-1440-02). The tubes were centrifuged at 2150 rpm for 30 minutes at room temperature and the interface layer was removed to a new tube and brought to a volume of 50 ml with PBS containing 2% FBS. The mixture was centrifuged for 10 minutes at 1200 rpm the supernatant was discarded, and the pellet was resuspended in 1 ml of PBS and placed on ice. The cells were counted to determine the concentration of natural killer (NK) cells, diluted to a concentration of $9.0 \times 10^4$ cells per 75 µL, and then 75 µL of these cells were then added to the Raji cells from the step above and then incubated for 4 hours at 37° C. The plate was then centrifuged at 1200 rpm for 5 minutes, and 100 µL of the supernatant was transferred to a flat, black clear-bottom 96 well plate and subsequently read on a Victor plate reader using a 490 nm excitation and 530 nm emission wavelength.

Figure 12:
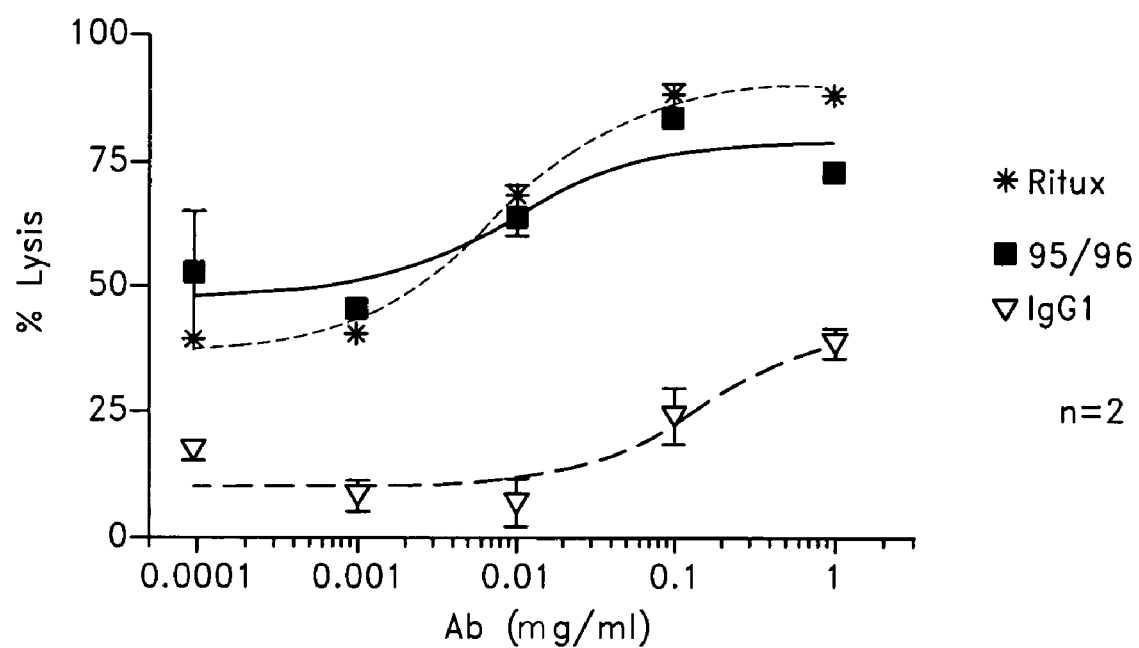
FIG. 12 is a line graph that shows the results of an assay that measures antibody dependent cellular cytotoxicity (ADCC) of Raji cells in the presence of either sc95/96, Rituximab, or control IgG1 antibody.

The results are shown in FIG. 12 and demonstrate that sc95/96 is able to induce Raji cell lysis by ADCC as did the positive control antibody Rituximab. This result indicates that one potential mechanism of action for sc95/96 is ADCC, which may have contributed to the efficacy of the antibody in vivo.

INCORPORATION BY REFERENCE

All references cited herein, including patents, patent applications, papers, text books, and the like, and the references cited therein, to the extent that they are not already, are hereby incorporated herein by reference in their entirety.

Equivalents

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A monoclonal antibody or binding fragment thereof that specifically binds to and neutralizes Matriptase catalytic domain; wherein said monoclonal antibody comprises:
   a) a heavy chain polypeptide comprising the sequence set forth in SEQ ID NO:4 and a light chain polypeptide comprising the sequence set forth in SEQ ID NO:6; or
   b) a heavy chain polypeptide comprising the sequence set forth in SEQ ID NO:8 and a light chain polypeptide comprising the sequence set forth in SEQ ID NO:10.

2. The monoclonal antibody or binding fragment of claim 1, in association with a pharmaceutically acceptable carrier.

3. The monoclonal antibody or binding fragment of claim 1, wherein said monoclonal antibody or binding fragment is linked to a therapeutic agent.

4. The monoclonal antibody or binding fragment of claim 3, wherein said therapeutic agent is a radionuclide.

5. The monoclonal antibody or binding fragment of claim 3, wherein the therapeutic agent is a toxin.

6. The monoclonal antibody or binding fragment of claim 1, wherein said monoclonal antibody or binding fragment does not generate a detectable human anti-human antibody (HAHA) immune response when administered to a human patient.

7. An assay kit for the detection of Matriptase in mammalian tissues or cells comprising the monoclonal antibody or binding fragment of claim 1 and an indicating means for detecting the binding of the monoclonal antibody or binding fragment with Matriptase when Matriptase is present.

8. The assay kit of claim 7, wherein the monoclonal antibody is a fully human monoclonal antibody.

9. The assay kit of claim 8, wherein the antibody is labeled.

10. The assay kit of claim 8, wherein the antibody is an unlabeled first antibody and the indicating means comprises a labeled second antibody that is an anti-immunoglobulin.

11. The assay kit of claim 8, wherein the antibody is labeled with a marker selected from the group consisting of a fluorochrome, an enzyme, a radionuclide and a radiopaque material.

12. The monoclonal antibody or binding fragment of claim 1, wherein said binding fragment is selected from the group consisting of Fab, Fab', F(ab')$_2$, and Fv.

13. The monoclonal antibody or binding fragment of claim 1, wherein said monoclonal antibody comprises a heavy chain polypeptide comprising the sequence set forth in SEQ ID NO:4 and a light chain polypeptide comprising the sequence set forth in SEQ ID NO:6.

14. The monoclonal antibody or binding fragment of claim 1, wherein said monoclonal antibody comprises a heavy chain polypeptide comprising the sequence set forth in SEQ ID NO:8 and a light chain polypeptide comprising the sequence set forth in SEQ ID NO:10.

15. An isolated nucleic acid molecule encoding one of the heavy chain polypeptide or the light chain polypeptide of element a) or b) of claim 1.

16. A vector comprising the nucleic acid molecule of claim 15.

17. An isolated host cell comprising the vector of claim 16.

* * * * *